(12) United States Patent
Smith et al.

(10) Patent No.: US 11,839,708 B2
(45) Date of Patent: Dec. 12, 2023

(54) LINEAR CARDIAC ASSIST PULSATILE PUMP

(71) Applicant: SummaCor, Inc., San Diego, CA (US)

(72) Inventors: Steve C. Smith, Trabuco Canyon, CA (US); Brian A. Babson, Long Beach, CA (US)

(73) Assignee: SummaCor, Inc., San Diego, CA (US)

( * ) Notice: Subject to any disclaimer, the term of this patent is extended or adjusted under 35 U.S.C. 154(b) by 460 days.

(21) Appl. No.: 17/073,085

(22) Filed: Oct. 16, 2020

(65) Prior Publication Data

US 2021/0113826 A1 Apr. 22, 2021

Related U.S. Application Data

(60) Provisional application No. 63/044,298, filed on Jun. 25, 2020, provisional application No. 62/923,542, filed on Oct. 19, 2019.

(51) Int. Cl.
*A61M 60/419* (2021.01)
*A61L 27/02* (2006.01)
(Continued)

(52) U.S. Cl.
CPC .......... *A61M 60/139* (2021.01); *A61M 60/13* (2021.01); *A61M 60/268* (2021.01);
(Continued)

(58) Field of Classification Search
CPC .. A61M 60/139; A61M 60/268; A61M 60/89; A61M 60/13; A61M 60/562; A61M 2205/0216
(Continued)

(56) References Cited

U.S. PATENT DOCUMENTS 1,959,106 A 5/1934 McSsing
3,464,359 A 9/1969 King et al.
(Continued)

FOREIGN PATENT DOCUMENTS

CN 108514661 A 9/2018
DE 19637723 A1 5/1997
(Continued)

OTHER PUBLICATIONS

International Search Report and Written Opinion dated Jul. 23, 2020, for International Application No. PCT/US2020/021591, 15 pages.
(Continued)

*Primary Examiner* — Erin M Piateski
(74) *Attorney, Agent, or Firm* — Cooley LLP

(57) ABSTRACT

Described herein are pumps that linearly reciprocate to assist with circulating blood within the body of a patient. Red blood cell damage may be avoided or minimized by such linear pump movement. The linearly reciprocating movement may also generate a pulsatile pumping cycle that mimics the natural pumping cycle of the heart. The pumps may be configured to reside at various body locations. For example, the pumps may be situated within the right ventricle, the left ventricle, the ascending aorta, the descending aorta, the thoracic aorta, or the abdominal aorta. In some instances, the pump may reside outside the patient.

96 Claims, 29 Drawing Sheets

(51) Int. Cl.
*A61M 60/139* (2021.01)
*A61M 60/13* (2021.01)
*A61M 60/562* (2021.01)
*A61M 60/89* (2021.01)
*A61M 60/268* (2021.01)

(52) U.S. Cl.
CPC .......... *A61M 60/562* (2021.01); *A61M 60/89* (2021.01); *A61M 2205/0216* (2013.01)

(58) Field of Classification Search
USPC .......................................................... 600/16
See application file for complete search history.

(56) References Cited

U.S. PATENT DOCUMENTS

| | | | |
|---|---|---|---|
| 3,791,769 | A | 2/1974 | Kovacs |
| 4,192,348 | A | 3/1980 | Hansen |
| 4,210,409 | A | 7/1980 | Child |
| 4,375,941 | A | 3/1983 | Child |
| 4,850,980 | A | 7/1989 | Lentz et al. |
| 4,925,377 | A | 5/1990 | Inacio et al. |
| 5,108,426 | A * | 4/1992 | Biro ................ A61M 60/892 |
| | | | 623/3.17 |
| 5,158,441 | A | 10/1992 | Aid et al. |
| 5,300,111 | A | 4/1994 | Panton et al. |
| 5,312,233 | A | 5/1994 | Tanny et al. |
| 5,368,439 | A | 11/1994 | Piazza |
| 5,443,503 | A | 8/1995 | Yamane |
| 5,456,715 | A | 10/1995 | Liotta |
| 5,674,281 | A | 10/1997 | Snyder |
| 5,676,651 | A | 10/1997 | Larson, Jr. et al. |
| 5,695,471 | A | 12/1997 | Wampler |
| 6,158,984 | A | 12/2000 | Cao et al. |
| 6,193,473 | B1 | 2/2001 | Mruk et al. |
| 6,201,329 | B1 | 3/2001 | Chen |
| 6,290,640 | B1 | 9/2001 | Goldowsky |
| 6,375,086 | B1 | 4/2002 | Babin et al. |
| 6,395,027 | B1 | 5/2002 | Snyder |
| 6,422,838 | B1 | 7/2002 | Sloteman |
| 6,436,027 | B1 | 8/2002 | Goldowsky |
| 6,511,298 | B2 | 1/2003 | Takura et al. |
| 6,511,413 | B2 | 1/2003 | Landesberg |
| 6,619,935 | B1 | 9/2003 | Kluth et al. |
| 6,723,039 | B2 | 4/2004 | French et al. |
| 6,969,345 | B2 * | 11/2005 | Jassawalla .......... A61M 60/531 |
| | | | 600/16 |
| 7,811,221 | B2 | 10/2010 | Gross |
| 7,850,593 | B2 | 12/2010 | Vincent et al. |
| 7,988,655 | B2 | 8/2011 | Rakhorst et al. |
| 8,157,720 | B2 | 4/2012 | Marseille et al. |
| 8,398,934 | B2 | 3/2013 | Bensley |
| 8,449,443 | B2 | 5/2013 | Rodefeld et al. |
| 8,574,291 | B2 | 11/2013 | Finocchiaro et al. |
| 8,597,350 | B2 | 12/2013 | Rudser et al. |
| 8,608,798 | B2 | 12/2013 | Wampler |
| 9,002,469 | B2 | 4/2015 | D'Ambrosio |
| 9,314,559 | B2 | 4/2016 | Smith et al. |
| 9,364,596 | B2 | 6/2016 | Vadala, Jr. et al. |
| 9,433,714 | B2 | 9/2016 | Voskoboynikov et al. |
| 9,433,716 | B2 | 9/2016 | Vadala, Jr. et al. |
| 9,446,180 | B2 | 9/2016 | Vadala, Jr. et al. |
| 9,555,173 | B2 | 1/2017 | Spanier |
| 10,188,779 | B1 | 1/2019 | Polverelli et al. |
| 10,279,094 | B2 | 5/2019 | Williams et al. |
| 10,398,821 | B2 | 9/2019 | Botterbusch et al. |
| 10,568,999 | B2 | 2/2020 | Gross |
| 11,617,875 | B2 | 4/2023 | Smith et al. |
| 2006/0030746 | A1 | 2/2006 | Grossmann |
| 2006/0245959 | A1 | 11/2006 | LaRose et al. |
| 2007/0237658 | A1 | 10/2007 | Burns et al. |
| 2007/0253842 | A1 | 11/2007 | Horvath et al. |
| 2008/0187449 | A1 | 8/2008 | Breidenbach |
| 2008/0294040 | A1 | 11/2008 | Mohiuddin et al. |
| 2009/0149950 | A1 | 6/2009 | Wampler |
| 2010/0109463 | A1 | 5/2010 | Jiang et al. |
| 2011/0201870 | A1 | 8/2011 | Forsell |
| 2012/0053557 | A1 | 3/2012 | Abal |
| 2012/0178986 | A1 | 7/2012 | Campbell et al. |
| 2012/0245678 | A1 | 9/2012 | Solem |
| 2013/0138205 | A1 | 5/2013 | Kushwaha et al. |
| 2014/0155998 | A1 | 6/2014 | Wampler |
| 2014/0179993 | A1 | 6/2014 | Alexander et al. |
| 2016/0045652 | A1 | 2/2016 | Cornen |
| 2018/0169316 | A1 * | 6/2018 | Lo ........................ A61M 1/16 |
| 2018/0207337 | A1 | 7/2018 | Spence et al. |
| 2019/0167877 | A1 | 6/2019 | Gross |
| 2019/0216995 | A1 | 7/2019 | Kapur et al. |
| 2019/0255236 | A1 | 8/2019 | Gross |
| 2019/0255237 | A1 | 8/2019 | Cinbis |
| 2019/0275225 | A1 | 9/2019 | Brown |
| 2019/0288565 | A1 | 9/2019 | Martinez et al. |
| 2019/0290819 | A1 | 9/2019 | Hansen |
| 2019/0323492 | A1 | 10/2019 | Tracey et al. |
| 2019/0358383 | A1 | 11/2019 | Reyes et al. |
| 2019/0365993 | A1 | 12/2019 | Staub et al. |
| 2019/0381227 | A1 | 12/2019 | Botterbusch et al. |
| 2020/0000999 | A1 | 1/2020 | Batchinsky et al. |
| 2020/0282119 | A1 | 9/2020 | Smith et al. |
| 2022/0072295 | A1 | 3/2022 | Smith et al. |
| 2022/0265989 | A1 | 8/2022 | Smith et al. |

FOREIGN PATENT DOCUMENTS

| | | |
|---|---|---|
| JP | S5279303 A | 7/1977 |
| WO | WO-2011069109 A2 | 6/2011 |
| WO | WO-2014140282 A1 | 9/2014 |
| WO | WO-2020185630 A1 | 9/2020 |
| WO | WO-2021077008 A1 | 4/2021 |
| WO | WO-2022051683 A1 | 3/2022 |
| WO | WO-2022178324 A1 | 8/2022 |

OTHER PUBLICATIONS

International Search Report and Written Opinion dated Feb. 8, 2021, for International Application No. PCT/US2020/056142, 11 pages.
Garbade et al., "Current Trends in Implantable Left Ventricular Assist Devices," Cardiology Research and Practice, vol. 2011, Article ID 290561, Mar. 1, 2011, 9 pages.
Patel, "Design and Development of a Pulsatile Axial Flow Blood Pump as a Left Ventricular Assist Device," Brunel Institute for Bioengineering, Brunel University, Dec. 2011, 209 pages.
Pulsatile Blood Pumps, product information p. 3 pages, https://www.harvardapparatus.com/catalog/product/view/id/8294/s/pulsatile-blood-pumps/category/515/, Retrieved May 17, 2021.
Extended European Search Report for European Application No. 20770326.5 dated Nov. 30, 2022, 5 pages.
International Preliminary Report on Patentability for International Application No. PCT/US2020/021591, dated Sep. 23, 2020, 13 pages.
International Preliminary Report on Patentability for International Application No. PCT/US2020/056142 dated Apr. 19, 2022, 7 pages.
International Preliminary Report on Patentability for International Application No. PCT/US2021/049166 dated Mar. 7, 2023, 11 pages.
International Search Report and Written Opinion for International Application No. PCT/US2021/049166, dated Dec. 20, 2021, 13 pages.
International Search Report and Written Opinion for International Application No. PCT/US2022/017098 dated Jun. 29, 2022, 18 pages.
Invitation to Pay Additional Fees for International Application No. PCT/US2022/017098 dated Apr. 19, 2022, 2 pages.

* cited by examiner

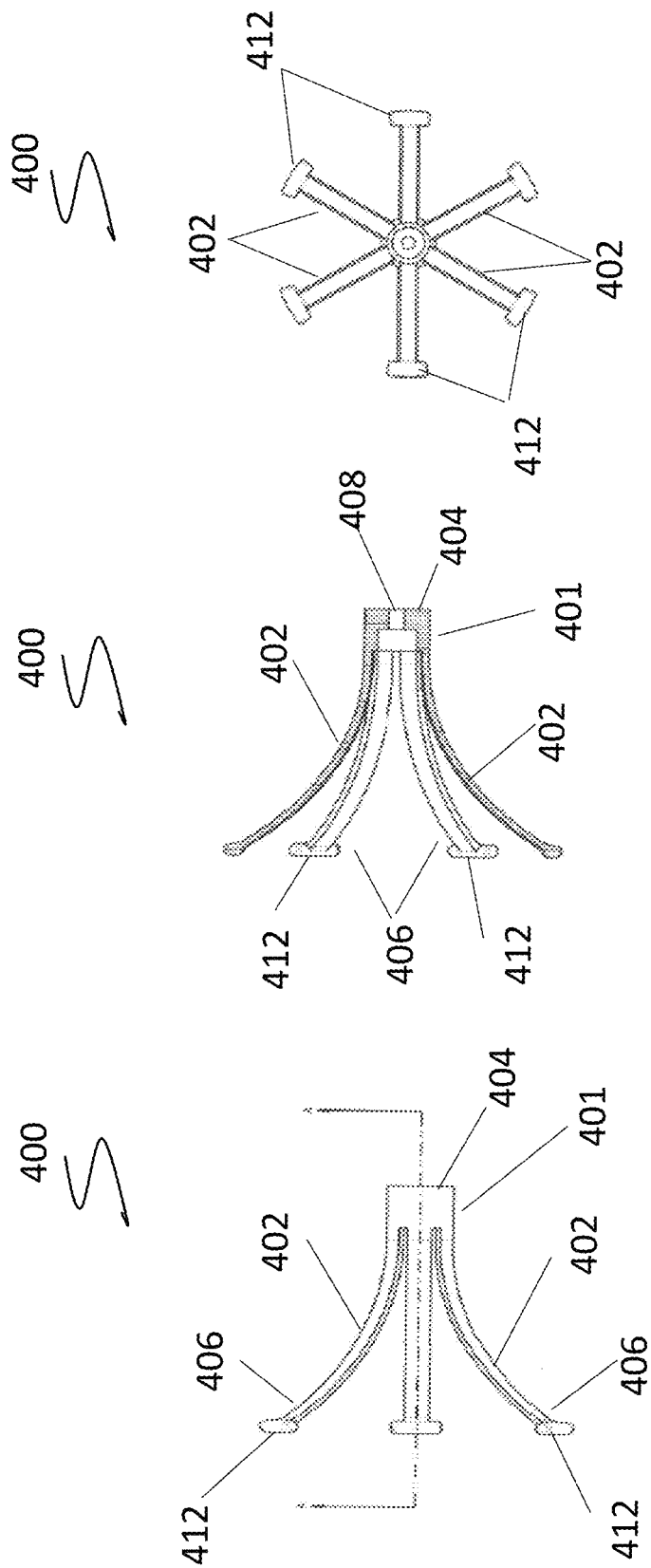

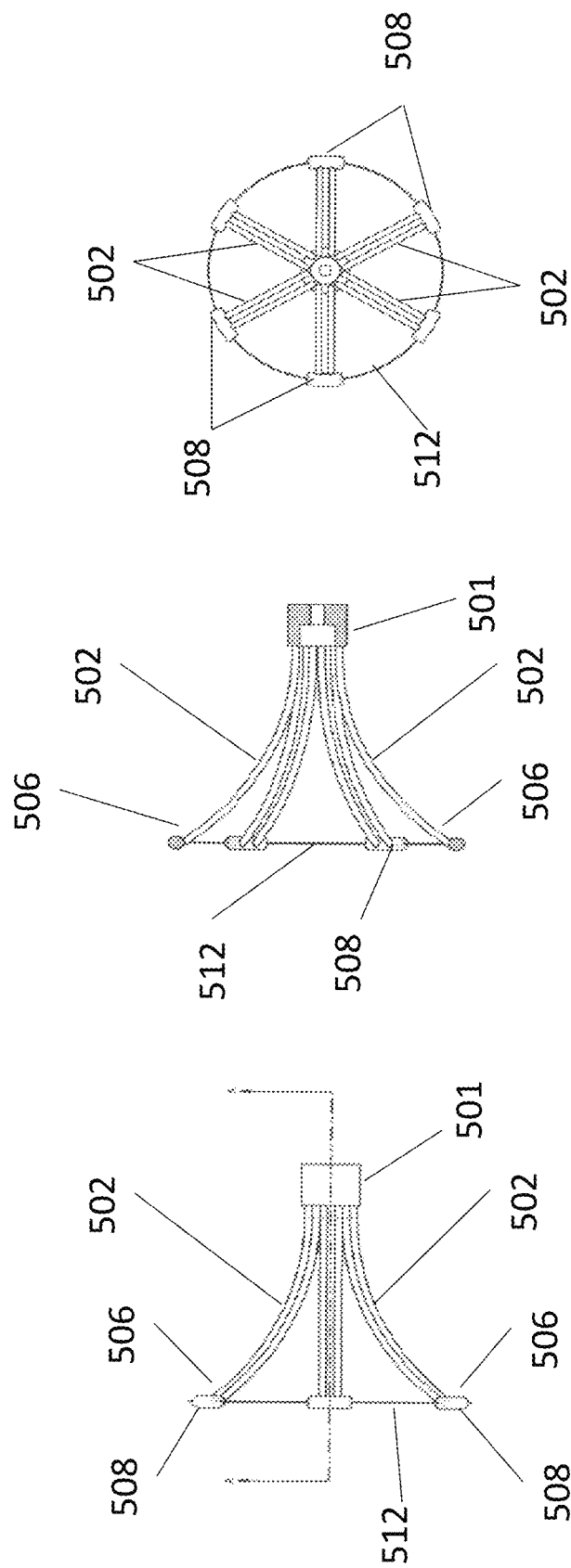

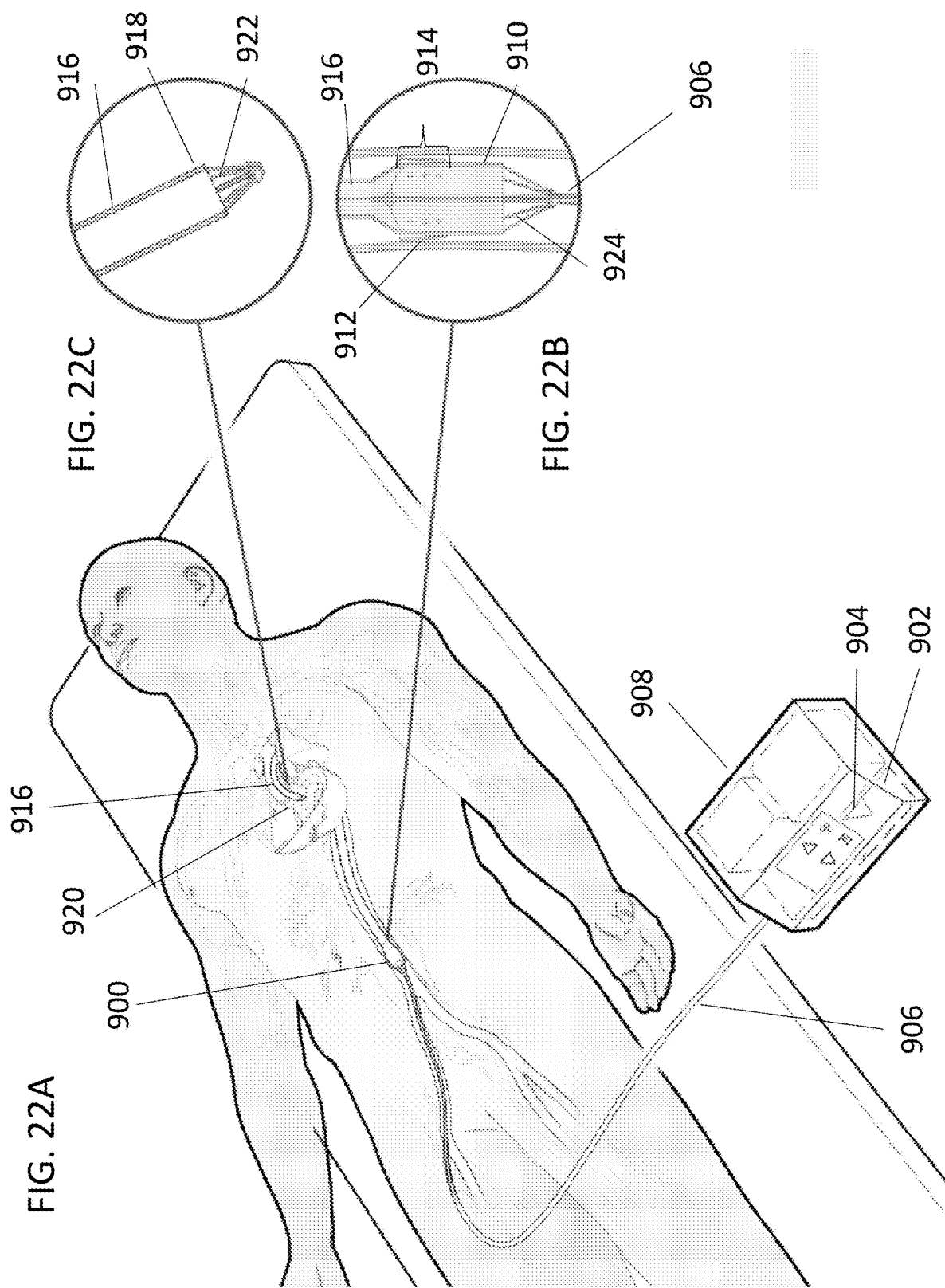

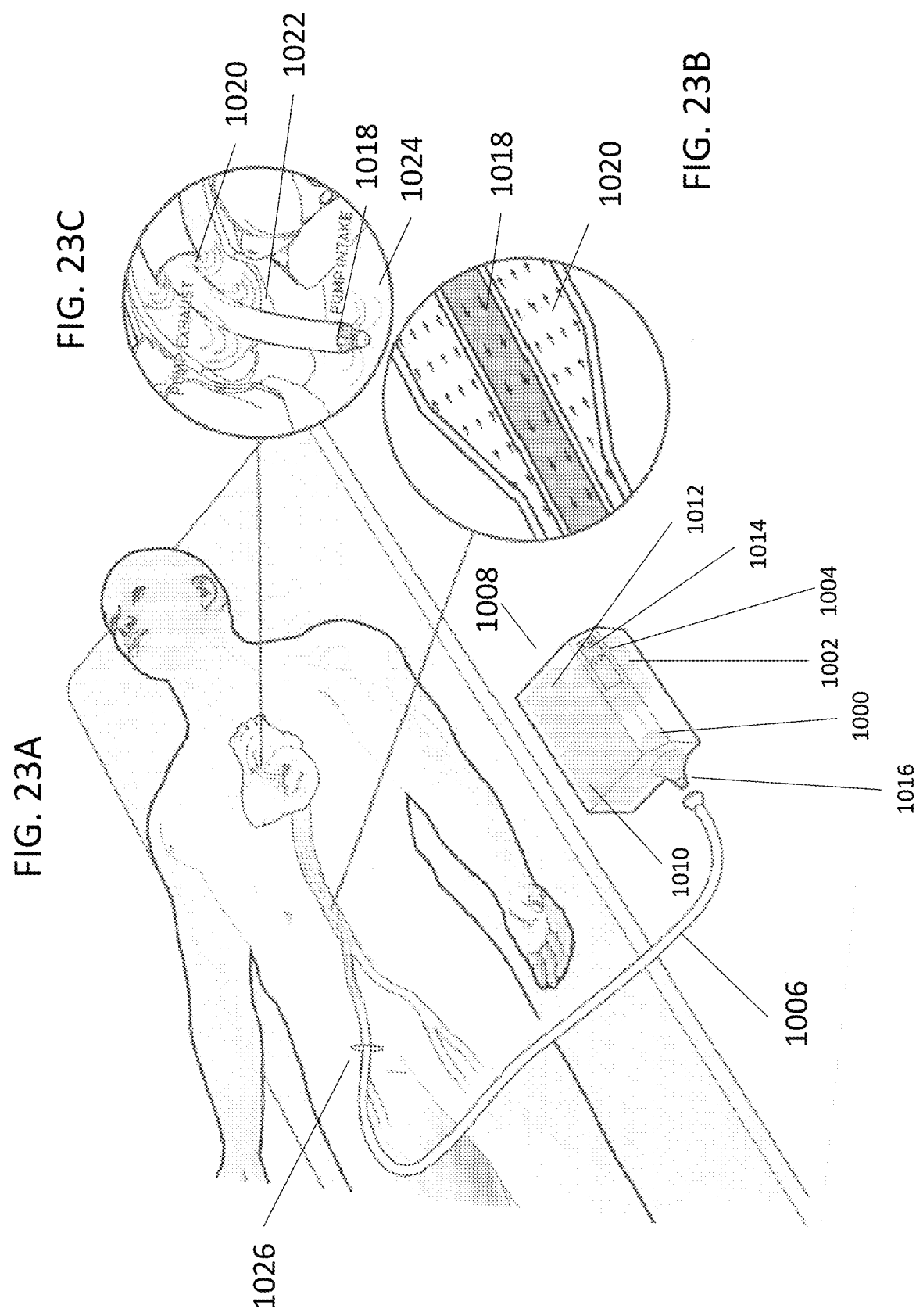

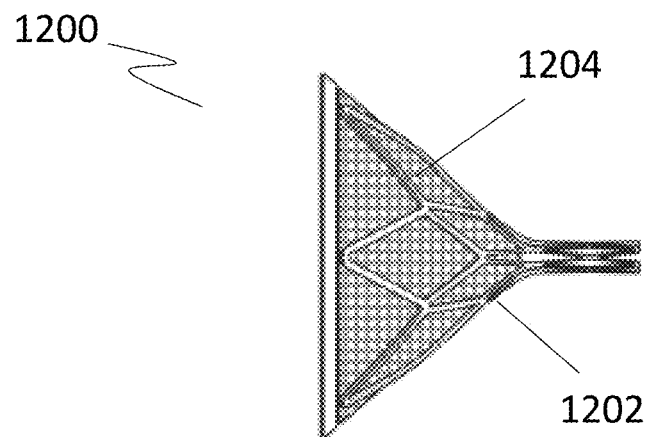
FIG. 25A
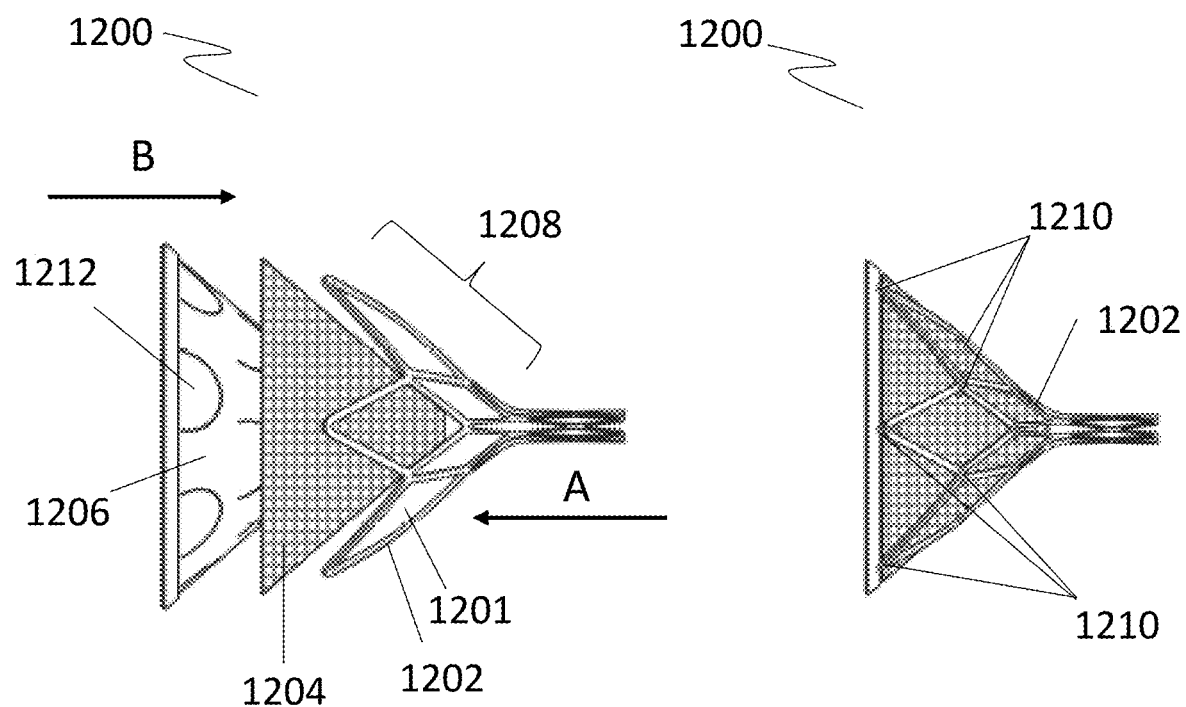
FIG. 25B
FIG. 25C

1

LINEAR CARDIAC ASSIST PULSATILE PUMP

CROSS-REFERENCE TO RELATED APPLICATIONS

This application claims priority to U.S. Provisional Application No. 62/923,542, filed on Oct. 19, 2019, and U.S. Provisional Application No. 63/044,298, filed on Jun. 25, 2020, each of which is hereby incorporated by reference in its entirety.

FIELD

This application relates generally to blood pumping devices. The devices may be cardiac assist devices or cardiac assist pumps of the type used to supplement or sustain blood flow on a short-term basis. Such devices are generally utilized in the treatment of patients experiencing compromised heart performance or heart failure in order to stabilize the patient and gain time for implementing more long-term treatment.

BACKGROUND

The treatment and survivability of patients experiencing severe heart trauma or heart failure is typically a time critical process. In most cases, the treatment of patients experiencing traumatic heart failure requires immediate life-sustaining measures. Basically, medical personnel must initially assist or stabilize the failing heart to maintain systemic circulation until further diagnostic measures are taken or treatment options decided.

While in some instances it may be possible for medical practitioners to stabilize such patients through careful administration of various drugs, the stabilization process often requires the application of a supplemental blood pumping apparatus. Such supplemental blood pumping apparatuses, known generally in the art as "cardiac assist devices" or "cardiac assist pumps" have had limited success despite the availability of various designs. These cardiac assist pumps generally utilize a small pumping apparatus, which is combined with a catheter support operatively coupled to an external pump drive and pump control system. The objective is to insert the pump into the patient's blood flow at a critical point in order to supplement or substitute for the pumping action of the patient's heart. While various pump design approaches have been employed, most cardiac assist pumps that have been developed include a rotary type pump such as a turbine impeller or the like.

Unfortunately, rotary type pumps have proven to be problematic for several reasons. Perhaps the most critical limitation of such pumps results from their undesired high speed of operation. Characteristically, such rotary pumps are required to be operated at higher rotational speeds in order to provide sufficient pressure and blood flow. Another drawback is that the use of high rotational speed pumps such as turbines, even on a short-term basis, causes damage to the patient's blood cells, which in turn endangers the patient's life. As a result, the operating time of cardiac assist pumps employing a rotational, turbine type pumping apparatus is typically limited. In addition to blood cell damage caused by high speed rotating pump apparatuses, problems also arise due to the constant unvarying flow characteristics of such rotational pumps. It has been found that the constant draw of a rotating pump may interfere with the action of heart valves and the pumping action of the heart.

2

Accordingly, it would be beneficial to have improved cardiac pump devices that avoid excessive damage to blood cells, and which are compatible with the pulsatile blood flow and pumping characteristics of the human heart.

SUMMARY

Described herein are pumps that linearly reciprocate to assist with circulating blood within the body of a patient. Red blood cell damage may be avoided or minimized by such linear pump movement. The linearly reciprocating movement may also generate a pulsatile pumping cycle resulting in a pulsatile blood flow that is compatible with the operation of the patient's heart. The pumps may be configured to reside at various body locations. For example, the pumps may be situated within the right ventricle, the left ventricle, the ascending aorta, the descending aorta, the thoracic aorta, or the abdominal aorta. In some instances, the pump may reside outside the patient.

In general, the pumps for assisting blood circulation described herein may include an expandable housing and a valve member disposed within the expandable housing that linearly reciprocates therein. The valve member may be, for example, a flexible diaphragm or a valve cone. Additionally, the valve members may include an inlet side that faces the inlet of the expandable housing, and an outlet side that faces the outlet side of the expandable housing. The expandable housing may include an interior surface and an expanded configuration, and may define a chamber for collecting blood. The flexible diaphragm may have an extended configuration and a collapsed configuration, and may include a diaphragm body and a rim. The valve cone may have an expanded configuration and a collapsed configuration, and may include a layer having a plurality of flaps that allow blood flow through the valve cone into the housing during the fill stroke, but which prevent blood flow through the valve cone during the pump stroke. In some instances, the pumps include a housing that is not expandable.

The valve members may be coupled to a support element having an expanded configuration and a collapsed configuration. The valve members may be structured such that expansion of the support element transforms the valve members to their expanded or extended configurations. In some variations, the support element may be an expandable frame having a conical shape. The expandable frame may be coupled to the actuator, and may support the valve cone or the flexible diaphragm as it linearly reciprocates within the housing. In other variations, the support element may be a tine support comprising a base and a plurality of tines coupled to the actuator that support the flexible diaphragm in the extended configuration during the pump stroke. The plurality of tines may be flexible and/or resilient, and have an expanded configuration and a compressed configuration.

The pumps may include an actuator coupled to the valve members (e.g., the flexible diaphragm or the valve cone), which may be configured to linearly reciprocate the valve members within the expandable housing to generate a fill stroke and a pump stroke of a pumping cycle. The rim of the valve members may be configured to maintain contact with the interior surface of the expandable housing during the pump stroke. In some variations, contact may be maintained for the entire duration of the pump stroke. In other variations, contact may be maintained for a portion of the pump stroke, as long as sufficient pressure is generated to move the desired amount of blood out of the housing during the pump stroke. In further variations, for example, when high pump speeds are required, the valve members may be configured such that there is a slight clearance or gap between the rim and the interior surface of the housing. The clearance gap may help to avoid the creation of undue friction in the pump. The clearance gap may also be sized so that adequate pressure may be generated for the pump stroke while also avoiding crushing or damaging red blood cells during the pump stroke. Here the diameter of the valve members in their extended or expanded configurations may be at least about 95 percent of the diameter of the housing in its expanded configuration. For example, the valve members in their extended or expanded configurations may be at least about percent 95 percent, at least about 96 percent, at least about 97 percent, at least about 98 percent, or at least about 99 percent of the diameter of the housing in its expanded configuration. The pumps may be driven by an external linear motor drive and linear motor controller situated at the end of a catheter external to the patient. The linear motor drive may be operatively coupled to the linearly acting cardiac assist pump by a flexible cable or other flexible actuator. A movable sleeve or sheath may hold the expandable housing and diaphragm or valve cone in a collapsed configuration to enable their insertion and advancement to a target location within the circulatory system.

More specifically, the expandable housing of the pump may comprise a support or scaffold including a proximal end and a distal end. The scaffold may be made from a material comprising stainless steel, titanium, or alloys thereof. With respect to the proximal and distal ends, they may or may not be tapered. Furthermore, the distal end of the scaffold may include an inlet for blood flow during the pump stroke. The proximal end of the scaffold may include an outlet for blood flow during the pump stroke.

In the expanded configuration, the expandable housing may have a diameter ranging from about 12 mm to about 20 mm. The expandable housing may further include a covering. For example, the expandable housing may include a polymer layer, which may comprise an elastomeric polymer such as, but not limited to, a silicone, a polyester, a polyurethane, or a combination thereof. Alternatively, the expandable housing may include a fabric layer coupled to the scaffold. For example, the fabric layer may comprise a woven material such as buckram or a material woven from polyester fibers. A film or sheet of non-woven material such as Mylar® plastic film may also be coupled to the expandable housing.

The pump may further include a cannula extending from the expandable housing. The cannula may extend from either the proximal end or the distal end of the expandable housing. The length of the cannula may vary, depending on such factors such as the intended location of pump placement, or the age or size of the patient. For example, cannula lengths may range from about 2.5 cm to about 5.0 cm, about 25 cm to about 30 cm, or about 35 cm to about 40 cm.

When the pump includes a valve cone within the expandable housing, the valve cone may include a plurality of material layers coupled to an expandable frame. The plurality of material layers may include mesh layers, flow control layers, or a combination thereof. In some instances, a mesh layer may be disposed between a flow control layer and the expandable frame. Woven fabrics or elastomeric polymers may be used to form the mesh layer. Exemplary elastomeric polymers include without limitation, a silicone, a polyester, a polyurethane, or a combination thereof. The material layers may be coupled to the expandable frame in any suitable manner, for example, by stitching, suturing, or embroidering, by use of an adhesive, by heat sealing, or by welding. The expandable frame may comprise stainless steel, nickel, titanium, or alloys thereof. In general, the valve cone has a conical shape, but any shape capable of being collapsed to permit advancement through the cannula may be used. When the valve cone is conically shaped, the plurality of material layers (e.g., the mesh and flow control layers) and the expandable frame in their expanded configurations are conically shaped. As previously mentioned, the valve cone may have an inlet side that faces the inlet of the expandable housing, and an outlet side that faces the outlet of the expandable housing.

The flow control layer of the valve cone may also be formed from various polymers, for example, an elastomeric polymer as stated above, or from Mylar® plastic film. The flow control layer may include a plurality of flaps having an open configuration and a closed configuration. In general, the plurality of flaps are in the open configuration during the fill stroke, and in the closed configuration during the pump stroke. The flow control layer may be cut to create a plurality of flaps, which may be of any suitable size and shape that allows blood to flow into the housing during the fill stroke. For example, the flaps may have a semi-circular shape, an arc shape, a circular shape, a triangular shape, a diamond shape, a square shape, or a rectangular shape. Any suitable number of flaps in the flow control layer may also be employed. For example, a flow control layer including 15 flaps may be useful. The valve cone may be configured such that a greater number of flaps are included when they are smaller in size, and a smaller number of flaps are included when they larger in size. When the flaps are semi-circular in shape, they may have a radius ranging from about 0.50 mm to about 3.0 mm, including all values and sub-ranges therein.

The mesh layer may be used to support the flow control layer such that when pressure against the flaps is applied during the pump stroke, the flaps are not pushed through the openings in the expandable frame. Thus, the mesh layer may help maintain the flaps in the closed configuration during the pump stroke when blood is moved out of the housing via the housing outlet. However, during the fill stroke, the mesh layer permits blood to flow from the housing inlet through the holes in the mesh and then through the flaps, transitioning them to their open configuration so that blood may move to the outlet side of the valve cone. In some instances, for example, when the openings of the expandable frame are smaller than the flaps, the valve cone may not include a mesh layer.

In addition to a rim, the flow control layer may include a body. The body and the rim may be made from the same material or from different materials. Additionally, the body and the rim may be separate components or integrally formed with one another. When provided as separate components, the body may be formed from an elastomeric polymer or from Mylar® plastic film, and the rim may be an O-ring. The peripheral edge of the flow control layer may be rolled over the O-ring to form the rim. The thickness of the rim may be greater than the thickness of the body. The body may have a thickness ranging from about 0.03 mm to about 0.05 mm. The rim may have a thickness ranging from about 0.20 mm to about 1.5 mm.

The flexible diaphragm contained within the expandable housing may comprise an elastomeric polymer. Non-limiting examples of elastomeric polymers include silicone, polyester, polyurethane elastomers, or a combination thereof. The body and rim of the flexible diaphragm may comprise the same material or different materials. In some instances, the diaphragm body and rim are integrally formed. Thicknesses of the diaphragm body may range from about 0.03 mm to about 0.3 mm. With respect to the rim of the diaphragm, its thickness may range from about 0.70 mm to about 1.5 mm. The thickness of the rim may be greater than the thickness of the diaphragm body, which may allow the flexible diaphragm to be in its collapsed configuration during the fill stroke, and the extended configuration during the pump stroke of a pumping cycle. However, in some variations, the rim and body may have equal thicknesses. The rim of the flexible diaphragm may have a width ranging from about 1 mm to about 2 mm.

Furthermore, the flexible diaphragm may have any suitable shape or geometry capable of creating a seal between the rim of the diaphragm and the interior surface of the expandable housing during the pump stroke. For example, the flexible diaphragm may have a conical shape when in the extended configuration. A plurality of ribs that extend from a center portion of the diaphragm body to the rim may be employed to maintain the conical shape during a pump stroke. The plurality of ribs may have a rib angle between a rib of the plurality of ribs and an axis perpendicular to the actuator that ranges from about 30 degrees to about 60 degrees. The plurality of ribs may be equally spaced from one another. In some variations, the plurality of ribs may have unequal spacing from one another. Some variations of the pump may also include a tine support comprising a base and a plurality of tines coupled to the actuator that support the flexible diaphragm in the extended configuration during the pump stroke. The plurality of tines may be flexible and/or resilient, and have an expanded configuration and a compressed configuration. In other variations, the flexible diaphragm may be coupled to an expandable frame that is conically shaped. Coupling to the expandable frame may be accomplished in any suitable manner, for example, by stitching, suturing, or embroidering, by use of an adhesive, by heat sealing, or by welding.

In some instances, the expandable housing of the pump may include a plurality of openings or perforations. The number of openings utilized may range between about 2 to about 25. The openings may be equally or unequally spaced on a portion of the expandable housing. Additionally, the plurality of openings may have a diameter ranging between about 0.10 mm to about 6.50 mm. When the expandable housing includes openings, a skirt may also be coupled to the expandable housing that surrounds the plurality of openings.

There are some variations in which the pump may be disposed within a console external to a patient. A coaxial catheter coupled the housing of the pump may provide continuous and pulsatile blood flow between the patient and the external pump, and have a diameter between about 1° F. and 18F. The coaxial catheter may include an inflow lumen and an outflow lumen. The inflow lumen may generally have a diameter greater than about 5 F.

Methods for pumping blood are further described herein. The methods generally include advancing a pump to a target location within the circulatory system of a patient, where the pump includes an expandable housing comprising an interior surface, an expanded configuration, and a collapsed configuration. The pump may further include a valve member that linearly reciprocates within the housing. Exemplary valve members may be a valve cone including a plurality of material layers coupled to an expandable frame, or a flexible diaphragm. The valve cone and flexible diaphragm may comprise a body and a rim, where the valve cone has an expanded configuration and a collapsed configuration, and the flexible diaphragm has an extended configuration and a collapsed configuration. Once at the target location, the expandable housing may be expanded to the expanded configuration and the valve cone or flexible diaphragm contained therein linearly reciprocated to generate a fill stroke and a pump stroke of a pumping cycle. During the pump stroke, contact between the rim of the valve cone or flexible diaphragm and the interior surface of the expandable housing may be maintained such that a seal is created to prevent blood flow between the rim and interior surface. Additionally, during the pump stroke, blood is pulled into the expandable housing. Depending on the variation of pump used, blood may be pulled into the expandable housing from the left ventricle or the aorta. The pump stroke may generally push blood out of the expandable housing into a portion of the aorta, for example, the ascending aorta or the descending aorta. During the pumping cycle, the flaps in the flow control layer of the valve cone close during the pump stroke and open during the fill stroke. When a flexible diaphragm is employed, it may be collapsed to the collapsed configuration during the fill stroke and extended to the extended configuration during the pump stroke.

The pump may be advanced and positioned in various parts of the circulatory system of the patient. For example, the expandable housing of the pump may be advanced through the aortic valve and into the left ventricle of the patient. When the pump further comprises a cannula, and the cannula may be advanced through the aortic valve and into the left ventricle of the patient. Non-limiting examples of target locations for the expandable housing include the aortic arch, the descending aorta, the thoracic aorta, and the abdominal aorta.

As previously described, the expandable housing may comprise a plurality of openings or perforations, and a skirt coupled to the expandable housing. In this instance, blood exiting the openings may be directed in a retrograde direction toward the heart of the patient during the pump stroke by the skirt. The length of the skirt may be adjusted to achieve a predetermined amount of retrograde blood flow toward the heart of the patient. The number of openings may also be adjusted to achieve a predetermined amount of retrograde blood flow toward the heart of the patient. Alternatively, the diameter of the openings may be adjusted to achieve a predetermined amount of retrograde blood flow toward the heart of the patient. Adjustment of any one or combination of the foregoing features may be utilized so that about 60% of the blood from the pump stroke flows in a retrograde direction toward the heart of the patient about 50% of the blood from the pump stroke flows in a retrograde direction toward the heart of the patient, or about 40% of the blood from the pump stroke flows in a retrograde direction toward the heart of the patient.

When the pump is disposed external to the patient, the method for pumping blood may include accessing the circulatory system of a patient with a coaxial catheter and coupling the coaxial catheter to the housing of the pump. The housing may comprise an interior surface. A flexible diaphragm contained within the housing may comprise a diaphragm body and a rim, where the flexible diaphragm has an extended configuration and a collapsed configuration. Alternatively, a valve cone may be disposed within the housing to linearly reciprocate therein. The external pump may be disposed within, or attached to, a console comprising a user interface.

Access to the circulatory system may be obtained from any suitable artery or vein, for example, the femoral artery, the subclavian artery, the carotid artery, or the jugular vein. Once access is obtained, the coaxial catheter may be advanced to a target location in the circulatory system and a valve member, for example, a valve cone or flexible diaphragm, linearly reciprocated within the expandable housing to generate a fill stroke and a pump stroke of a pumping cycle. During the pump stroke, contact between the rim of the valve cone or the flexible diaphragm and the interior surface of the expandable housing may be maintained to create a seal therebetween and prevent blood from flowing around the flexible diaphragm. The seal may help generate and maintain the force of the pump stroke as well as minimize red blood cell damage that may occur with blood flowing between a space existing between the rim and the interior surface. The methods described herein may include advancing coaxial catheter to various target locations in a patient. For example, the target location for the inflow lumen may a left ventricle of the patient, or the target location for the outflow lumen may be above an aortic valve of the patient.

The coaxial catheter may comprise an inflow lumen and an outflow lumen. The inflow lumen may receive blood from the left ventricle and the outflow lumen may return blood to the ascending aorta. In general, the pump stroke may pull blood into the housing through the inflow lumen as well as push blood out of the housing and through the outflow lumen. During the fill stroke, the flexible diaphragm may be collapsed to the collapsed configuration. Correspondingly, the flexible diaphragm may be extended to the extended configuration during the pump stroke. When a valve cone is used, the plurality of flaps in the flow control layer may be open during the fill stroke and closed during the pump stroke. A mesh layer may be provided with the flow control layer to support the flaps and prevent them from opening during the pump stroke.

Other methods for pumping blood may include advancing a pump to a target location within the aorta of a patient, such as the thoracic aorta or the abdominal aorta, where the pump has a fill stroke and a pump stroke; pulling a fill volume of blood into the pump during the pump stroke; and pushing an exit volume of blood out of the pump during the pump stroke, where the exit volume comprises a first portion of blood and a second portion of blood. The fill stroke may pull blood from the left ventricle of the patient. Additionally, the first portion of blood may be pumped in a retrograde direction toward the head of the patient, and the second portion of blood may be pumped in an anterograde direction. The second portion of blood may be about 60% of the exit volume, about 50% of the exit volume, or about 40% of the exit volume.

In some methods, an expandable housing having a cannula extending from a proximal end of the housing is advanced within a selected artery and positioned at a target location, such as the patient's aorta and left ventricle. The selected artery may be the femoral artery. Once at the target location, a sheath surrounding the expandable housing may be withdrawn, thereby allowing the expandable housing to expand to its pumping configuration. An actuator may then be advanced into the housing and a linear motor drive activated to induce reciprocating motion of a valve member (e.g., a valve cone or a flexible diaphragm) coupled thereto within the expandable housing in forward and rearward directions. During the reciprocating movement, forward movements may induce blood flow into the housing and rearward movements may exert a pumping force against blood within the housing. The result is a linear pulsatile pumping action that may be extremely efficient, and which may be compatible with the pulsatile behavior of the human heart. The characteristics of the reciprocating movement of the pumps described herein may be independently varied to provide optimized forward strokes, rearward strokes, and movement profiles.

BRIEF DESCRIPTION OF THE DRAWINGS

In FIG. 10C, the scaffold is shown coupled to the blocking layer.

FIG. 12A shows a top view of flexible diaphragm and FIG. 12B shows a side, cross-sectional view of the diaphragm in FIG. 12A taken along line A-A.

FIGS. 13A-13C depict enlarged views of a plurality of tines according to one variation. FIG. 13A shows a side view of the plurality of tines; FIG. 13B shows a side, cross-sectional view of the tines of FIG. 13A taken along line A-A; and FIG. 13C shows a front view of the tines of FIG. 13A, illustrating their spacing from one another.

FIGS. 14A-14C depict enlarged views of another exemplary design for the plurality of tines. FIG. 14A shows a side view of the plurality of tines; FIG. 14B shows a side, cross-sectional view of the tines of FIG. 14A taken along line A-A; and FIG. 14C shows a front view of the tines of FIG. 14A, illustrating their spacing from one another.

FIG. 16A shows a top view of the diaphragm of FIG. 15; FIG. 16B shows a side view of the diaphragm of FIG. 16A, and FIG. 16C shows a side, cross-sectional view of the diaphragm of FIG. 16B.

FIG. 18A shows the pump positioned in the descending thoracic portion of the aorta. FIG. 18B shows the pump positioned in the descending abdominal portion of the aorta.

FIGS. 22A-22C depict a pump according to yet another variation, coupled to a linear motor drive external to the patient. FIG. 22A shows the pump within the patient and coupled to the linear motor drive within an external console; FIG. 22B shows a close-up view of the housing of the pump within the patient; and FIG. 22C shows a close-up view of the distal end of the cannula within the left ventricle.

FIGS. 23A-23C depict an exemplary external pump disposed within a bedside console, coupled to the patient via a coaxial catheter. FIG. 23A shows the coaxial catheter within the patient and coupled to linear motor drive within a bedside console; FIG. 23B shows a close-up view of the inflow and outflow lumens of the coaxial catheter; and FIG. 23C shows a close-up view of the inlet and outlet of the coaxial catheter.

FIG. 24A shows a perspective view of the pump and pressure sensors; FIG. 24B shows an enlarged view of two pressure sensors at the outlet of the pump; and FIG. 24C shows an enlarged view of two pressure sensors at the inlet of the pump.

FIGS. 25A-25C depict an exemplary valve member including an expandable frame, a mesh cone, and a flow control cone. FIG. 25A shows the mesh cone and the flow control cone coupled to the expandable frame; FIG. 25B shows an assembly view of the expandable frame, mesh cone, and flow control cone; and FIG. 25C shows the mesh cone and flow control cone stitched to the expandable frame at multiple attachment points.

FIG. 26A shows a perspective view of the expandable frame; FIG. 26B shows a side view of the expandable frame; and FIG. 26C shows a top view of the expandable frame.

FIG. 27A shows a circular piece of mesh including a free edge, which may be rolled into the cone shape shown in FIG. 27B.

FIG. 28A shows a circular piece of material including a plurality of flaps and a free edge; FIG. 28B shows a rim running circumferentially about the periphery of the material; and FIG. 28C shows the circular piece of material rolled into a cone shape.

DETAILED DESCRIPTION

Figure 1:
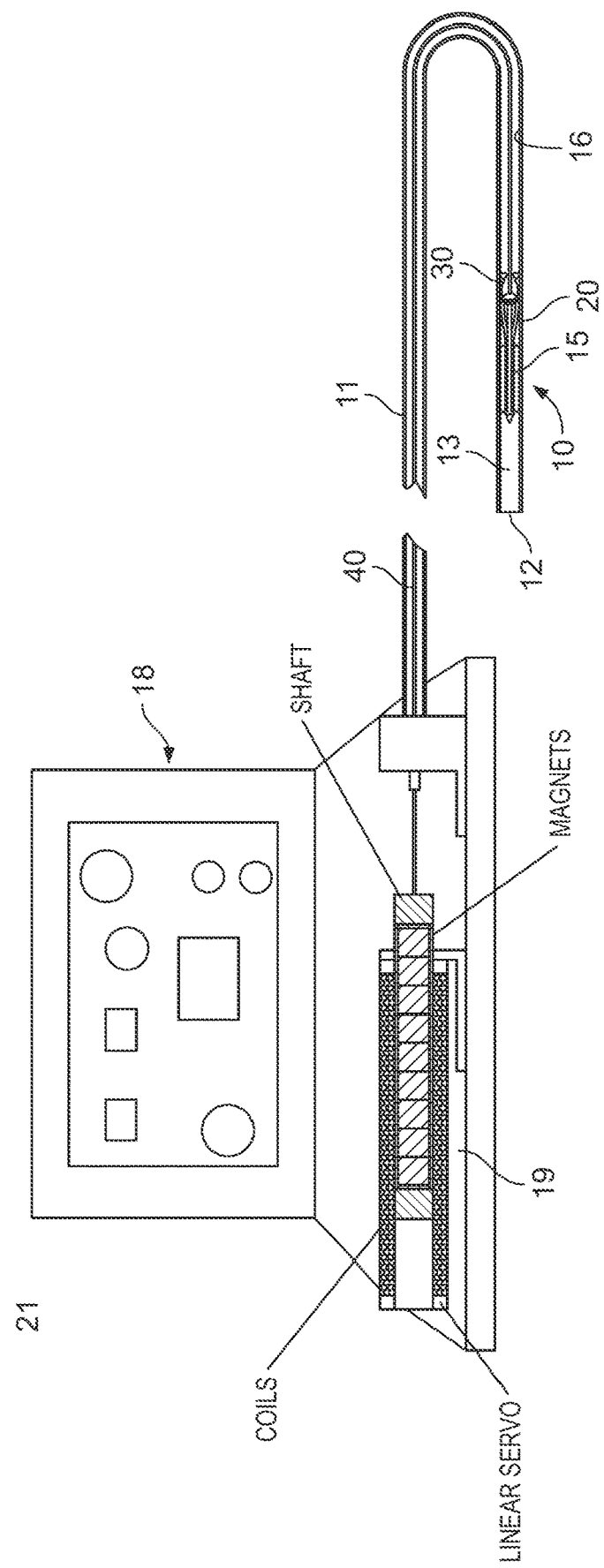
FIG. 1 depicts a perspective view of an exemplary pump and linear motor drive.

Described herein are pumps for assisting blood circulation. Instead of a rotary impeller, the pumps may include a linearly reciprocating member to move blood, which may help avoid the shear forces that cause red blood cell damage, and which pumps blood in a pulsatile fashion, mimicking the natural pumping cycle of the heart. The pumps may create a pressure wave or back pulse during the fill stroke to assist with the operation of the associated heart and may eliminate the collapse of blood vessels. Furthermore, the pumps may be able to provide adequate blood flow at operational speeds between 50 and 500 cycles per minute, which provides very slow movement compared to rotary impellers, and which may prevent red blood cell hemolysis. With slower pump speeds, less heat may be generated than rotary impellers, avoiding the need to include cooling apparatuses.

The linearly reciprocating member may include a valve member constructed such that a seal is created between it and the housing during a pump stroke of the pumping cycle, thereby generating the blood pressure needed to move blood peripherally. The pump stroke and length of the linearly reciprocating member, as well as the stroke speed, may be independently adjustable. Blood pressure and blood flow rate may be controlled by stroke length and speed adjustments. Furthermore, adjustable front and back stroke speed ramping may avoid a jolt within the pressure characteristics of the circulatory system. The pumps may be placed in various parts of the circulatory system of a patient, such as the left ventricle, the right ventricle, and the aorta. However, in some instances it may be useful to have the pump external to the patient.

Pumps

The pumps for assisting blood circulation described herein may include a housing and a linearly reciprocating member that comprises a valve member, for example, a flexible diaphragm or valve cone, disposed within the housing. The housing may be expandable and include an interior surface, an expanded configuration, and a collapsed configuration. A sheath, which may be concentrically disposed about the housing, may maintain the housing in the collapsed configuration during advancement to a target location. Upon reaching the target location, the sheath may be retracted to allow expansion of the housing to the expanded configuration. Additionally, the flexible diaphragm may have an extended configuration and a collapsed configuration, and may include a diaphragm body and a rim. Likewise, the valve cone may have an expanded configuration and a collapsed configuration, and may include a layer having a plurality of flaps that allow blood flow into the housing during the fill stroke but prevents blood flow through the valve cone during the pump stroke. A bearing within the expandable housing may also be provided to contain movement of the flexible diaphragm or valve cone within the housing.

The pumps may also include an actuator coupled to the flexible diaphragm or valve cone via a support element, which may be configured to linearly reciprocate the flexible diaphragm or valve cone within the housing to generate a fill stroke and a pump stroke of a pumping cycle. The rim of the flexible diaphragm or the valve cone may be configured to maintain contact with the interior surface of the housing during the pump stroke. However, the support elements may generally be sized and/or shaped so that they do not contact the inside surface of the housing while they linearly reciprocate within the housing. The pumps may be driven by an external linear motor drive and linear motor controller, which may be situated at the proximal end of a catheter external to the patient. The linear motor drive may be operatively coupled to the pump by a cable or other actuator. Furthermore, the pumps may be powered by AC or DC sources.

Housing

In general, the housing of the pump comprises a body, a proximal end, and a distal end. Additionally, the housing may be expandable and include an expanded configuration and a collapsed configuration, as previously stated. The housing may define a chamber for collecting and holding blood until moved out by a pump stroke, and may comprise a support or scaffold and a covering. The housing may be advanced to a target location within the circulatory system of a patient in the collapsed configuration. Upon reaching the target location, the housing may then be expanded to the expanded configuration to provide a chamber for collection of the blood to be pumped. The housing may have a diameter ranging from about 12 mm to about 20 mm in its expanded configuration, including all sub-ranges therein. For example, the housing may have a diameter of about 12 mm, about 13 mm, about 14 mm, about 15 mm, about 16 mm, about 17 mm, about 18 mm, about 19 mm, or about 20 mm in its expanded configuration. The diameter may be selected based on such factors as the location at which the housing will reside, the age of the patient, and whether other features, e.g., a cannula, coaxial catheter, skirt, etc., are utilized with the housing.

The support or scaffold may also include a proximal end and a distal end. The scaffold may be formed from braided, woven, and/or coiled filaments, and may be made from various materials. For example, scaffold materials may include biocompatible polymers and metals comprising stainless steel, titanium, or alloys thereof. For example, the scaffold may comprise a nickel-titanium alloy (Nitinol). With respect to the proximal and distal ends of the scaffold, they may be tapered, blunt, or straight. Furthermore, the distal end of the scaffold may include an inlet for blood flow during the pump stroke. The proximal end of the scaffold may include an outlet for blood flow during the pump stroke. In one variation, the scaffold may be a self-expanding stent.

The housing may further comprise a covering or layer configured to block the flow of blood. The covering or layer may be provided on the entire scaffold or on a section or portion of the scaffold. In one variation, the covering or layer may comprise a polymer, and may thus form a polymer layer. The polymer layer may be overmolded on the scaffold such that scaffold is embedded within the polymer layer. In some variations, the scaffold may be positioned within the center of the polymer layer, while in other variations, the scaffold may be positioned toward an inner or outer edge of the polymer layer. Embedding or otherwise entirely covering the scaffold with the polymer layer may provide the expandable housing with a smooth interior surface. The polymer layer may comprise an elastomeric polymer such as, but not limited to, silicone, polyester, polyurethane, or a combination thereof. Alternatively, the covering or layer may comprise a fabric, and may thus form a fabric layer. In these variations, the expandable housing may include a fabric layer coupled to the scaffold, usually to an interior surface of the scaffold. The fabric layer may be coupled to the scaffold by any suitable means, such as, for example stitching the fabric layer to the scaffold at one or more points (e.g., a plurality). The stitch points may be specifically selected such that the fabric layer forms a smooth surface (e.g., on the interior of the housing) so as not to disrupt the interface between the flexible diaphragm and the housing. In other variations, the fabric layer may be coupled to the scaffold using an adhesive such as an acrylic adhesive, a cyanoacrylate adhesive, or a silicone adhesive. Non-limiting examples of materials that may be used as the fabric layer include a woven material such as buckram or a material woven from polyester fibers. A film or sheet of non-woven material such as Mylar® plastic film may also be used.

In some instances, the housing of the pump (e.g., the covering or layer) may include a plurality of openings or perforations. The number of openings utilized may range from about 2 to about 25, including all values and sub-ranges therein. For example, the expandable housing may include 2 openings, 3 openings, 4 openings, 5 openings, 6 openings, 7 openings, 8 openings, 9 openings, 10 openings, 11 openings, 12 openings, 13 openings, 14 openings, 15 openings, 16 openings, 17 openings, 18 openings, 19 openings, 20 openings, 21 openings, 22 openings, 23 openings, 24 openings, or 25 openings. The openings may be equally or unequally spaced on a portion of the housing, and/or arranged in a pattern on a portion of the housing. Additionally, the plurality of openings may have a diameter ranging from about 0.10 mm to about 6.50 mm, including all values and sub-ranges therein. For example, the diameter may be about 0.10 mm, about 0.5 mm, about 1.0 mm, about 1.5 mm, about 2.0 mm, about 2.5 mm, about 3.0 mm, about 3.5 mm, about 4.0 mm, about 4.5 mm, about 5.0 mm, about 5.5 mm, about 6.0 mm, or about 6.5 mm. The plurality of openings in the expandable housing may have the same diameter or different diameters. Furthermore, the plurality of openings may have any suitable shape, for example, circular, ovoid, or slot-like. In variations comprising slots, the slots may be linear, v-shaped, or arcuate in shape. In one variation, the housing includes four openings evenly spaced about the housing.

When the housing includes openings or perforations, a skirt may be coupled to the expandable housing in a manner that covers, surrounds, or otherwise overlies the plurality of openings to assist in generating retrograde blood flow directed toward the patient's head during the pump stroke of a pumping cycle. The retrograde blood flow may help provide adequate perfusion of arteries branching from the aortic arch, for example, the carotid arteries and subclavian arteries. The ability to maintain adequate perfusion of the subclavian artery may prevent flow reversal from the vertebrobasilar artery to the subclavian artery, a phenomenon known as "subclavian steal." The combination of the number of openings and opening diameter may provide an amount of open surface area on the housing for retrograde blood flow. Additionally, the skirt may be configured to adjust the amount of open surface area for retrograde flow by adjusting the number of patent (open) and closed openings. In general, a larger amount of open surface area may provide more retrograde blood flow toward the head and heart of the patient, and a smaller amount of open surface area may provide a greater amount of anterograde blood flow to the body. In some variations, a mechanism that lifts, opens, or flares the skirt off the external surface of the housing may be provided. For example, a tether may be coupled to the skirt, e.g., around the external surface of the skirt, and configured to open and close the skirt against the housing similar to how a noose can be tightened and loosened. The amount of opening or closing may be adjusted using a rotatable dial disposed, e.g., on a console external to the patient.

The skirt may have any suitable shape that directs blood back toward the head and heart (e.g., cylindrical or frusto-conical), and may be coupled to the housing in various ways. In one variation, the skirt may be a separate component from the housing and may be attached to the housing by any suitable means, such as, for example, friction fit or using an adhesive. In another variation, the skirt may be integral with the housing (e.g., the two may be formed integrally, such as, by molding the two as a single component). The skirt may be made from the same materials as the housing. For example, the skirt may comprise a mesh made from stainless steel, titanium, or alloys thereof (e.g., Nitinol), and a polymer or fabric layer. The length of the skirt may also vary, and range from about 0.32 cm (0.125 inch) to about 1.90 cm (0.750 inch).

Cannula

In some variations, the pumps may include a cannula comprising an elongate body, a proximal end, a distal end, and a lumen running therethrough. The cannula may be coupled to the housing as a separate component, or be integrally formed as an extension thereof. Depending on the placement of the housing, the cannula may be coupled or extend from the proximal or distal end of the housing. For example, when the housing resides within the left ventricle, a cannula may extend from the proximal end of the housing such that it traverses the aortic valve and extends into the ascending aorta. In other variations, the pumps may include a cannula extending from the distal end of the housing. For example, when the housing resides in the aorta, a cannula may extend from the distal end of the housing such that it traverses the aortic valve to extend into the left ventricle. In further variations, the housing may not have a cannula extending therefrom. In these instances, the housing may reside within any portion of the aorta, for example, the thoracic aorta or the abdominal aorta.

Cannulas of various lengths may be used. For example, short, medium, or long cannulas may be used. When a short cannula is employed, the length of the cannula may range from about 2.5 cm to about 5.0 cm, including all values and sub-ranges therein. For example, the length of the short cannula may be about 2.5 cm, about 3.0 cm, about 3.5 cm, about 4.0 cm, about 4.5 cm, or about 5.0 cm. When a medium length cannula is used, the length of the cannula may range from about 25 cm to about 30 cm, including all values and sub-ranges therein. For example, the length of the medium cannula may be about 25 cm, about 26 cm, about 27 cm, about 28 cm, about 29 cm, or about 30 cm. When a long cannula is used, the length of the cannula may range from 35 cm to about 40 cm, including all values and sub-ranges therein. For example, the long cannula may be about 35 cm, about 36 cm, about 37 cm, about 38 cm, about 39 cm, or about 40 cm. In some variations, a pump may be provided with each of a short, a medium, and a long cannula and a user may select the appropriate cannula based on desired use of the pump. It should be appreciated, that in some instances, other cannula lengths may also be used.

Coaxial Catheter

As mentioned above, in some variations the pump may be disposed external to the body, for example, within a console at the patient's bedside. In these variations, the pump may further comprise a coaxial catheter. A first end of the coaxial catheter may be coupled to the housing of the pump via a connector or adapter and the opposite (second) end of the coaxial catheter may be inserted into the patient such that blood flows between the patient and the housing. The coaxial catheter may have an outside diameter between about 1° F. and about 18 F, including all values and sub-ranges therein. For example, the outside diameter of the coaxial catheter may be about 10 F, about 11 F, about 12 F, about 13 F, about 14 F, about 15 F, about 16 F, about 17 F, or about 18 F. The coaxial catheter may include an inflow lumen and an outflow lumen. In some variations, the outflow lumen may be concentrically disposed about the inflow lumen. In other variations, the inflow and outflow lumens may extend parallel to one another within the coaxial catheter. The inflow lumen may generally have an internal diameter between about 7 F and about 14 F.

The inflow and/or outflow lumens of the coaxial catheter may be flushed, e.g., with sterile saline or heparinized saline. Flushing may be performed at any time, but is generally performed prior to use of the coaxial catheter. The fluid for flushing the coaxial catheter may be introduced into one or more of the catheter lumens by various types of connectors, for example, Y connectors or two or three way connectors. Other types of catheter connectors and fittings may also be used. Flushing around the coaxial catheter site may also be performed around the site of insertion into the body.

Valve Cone

The linearly reciprocating member of the pumps described herein may include a valve member such as a valve cone. The valve cone may be disposed within the expandable housing and may include a plurality of material layers coupled to a support member. The support member may be an expandable frame. However, in some variations, a single layer of material may be coupled to the support member. As previously mentioned, the valve cone may have an inlet side that faces the inlet of the expandable housing, and an outlet side that faces the outlet of the expandable housing. The plurality of material layers may include mesh layers, flow control layers, or a combination thereof. Any number of material layers may be used, as long as at least one flow control layer is included. The flow control layer generally includes a plurality of flaps that open when blood is pulled into the expandable housing during the fill stroke, and which close when blood is moved out of the expandable housing during the pump stroke. The mesh layer may be disposed between the flow control layer and the expandable frame and used to support the flow control layer such that when pressure against the flaps is applied during the pump stroke, the flaps are not pushed or bent through the openings in the expandable frame. Thus, the mesh layer may help maintain the flaps in the closed configuration during the pump stroke when blood is moved out of the housing via the housing outlet. However, during the fill stroke, the mesh layer permits blood to flow from the housing inlet through the holes in the mesh and then through the flaps, transitioning them to their open configuration so that blood may move to the outlet side of the valve cone.

Woven fabrics or elastomeric polymers may be used to form the mesh layer. Exemplary elastomeric polymers include without limitation, a silicone, a polyester, a polyurethane, or a combination thereof. The thickness of the mesh layer may range from about 0.03 mm to about 0.05 mm, including all values and sub-ranges therein. The size and shape of the mesh openings may also vary and may depend on the size and shape of the flaps in the flow control layer given their supportive function, as described above. With respect to shape, the mesh openings may be circular, triangular, square, rectangular, or diamond shaped, etc.

The material layers may be coupled to the expandable frame in any suitable manner, for example, by stitching, suturing, or embroidering, by use of an adhesive, by heat sealing, or by welding. The material layers may be coupled to the expandable frame at a plurality of attachment points on the frame. The expandable frame may have an expanded configuration and a collapsed configuration, and comprise stainless steel, nickel, titanium, or alloys thereof (e.g., nitinol). In one variation, the expandable frame is made from a laser cut nitinol tube. The expandable frame may have a first end that couples to the actuator of the pump, and a shaped second end that couples to the material layers of the valve cone. In general, the shape of the valve cone corresponds to the shape of the expandable frame. Although the expandable frame typically has a conical shape, any shape capable of being collapsed to permit advancement through the cannula may be used. When the expandable frame is conically shaped, the plurality of material layers (e.g., the mesh and flow control layers) may also be conically shaped.

The flow control layer of the valve cone may also be formed from various polymers, for example, an elastomeric polymer as stated above, or from Mylar® plastic film. The flow control layer may include a plurality of flaps having an open configuration and a closed configuration. In general, the plurality of flaps are in the open configuration during the fill stroke, and in the closed configuration during the pump stroke. The flow control layer may be cut to create a plurality of flaps, which may be of any suitable size and shape that allows blood to flow into the housing during the fill stroke. For example, the flaps may have a semi-circular shape, an arc shape, a circular shape, a triangular shape, a diamond shape, a square shape, or a rectangular shape. Any suitable number of flaps in the flow control layer may also be employed. The number of flaps may range from 2 to 20. For example, 2 flaps, 3 flaps, 4 flaps, 5 flaps, 6 flaps, seven flaps, 8 flaps, 9 flaps, 10 flaps, 11 flaps, 12 flaps, 13 flaps, 14 flaps, 15 flaps, 16 flaps, 17 flaps, 18 flaps, 19 flaps, or 20 flaps may be included. In one variation, a flow control layer including 15 flaps may be useful. The valve cone may be configured such that a greater number of flaps are included when they are smaller in size, and a smaller number of flaps are included when they larger in size. When the flaps are semi-circular in shape, they may have a radius ranging from about 0.50 mm to about 3.0 mm, including all values and sub-ranges therein.

When the cone valve is conically shaped, the flow control layer is generally also conically shaped. Here the material of the flow control layer may first be provided as a circle with center cut out and a slit extending from the cut out to the periphery of the circle (e.g., see 28A). The slit provides a free edge so that the layer may later be rolled to form a cone shape. Next, the flaps may be formed by laser cutting or stamping the flap shapes into the flow control layer. The flaps may have any suitable size and shape, as previously stated. In one variation, a rim is then created at the periphery of the circle by rolling the edge of the flow control layer upon itself to create thickness at the periphery and stitching, heat sealing, gluing, etc., the rolled edge to maintain the thickness in that area. In another variation, the edge may be rolled over an O-ring to form the rim. In a further variation, the rim is a separate component from the flow control layer, and includes an O-ring that is stitched, heat sealed, glued, bonded, etc., to the edge of the flow control layer. After the rim is formed, a free edge of the circular flow control layer is rolled to shape it into a cone. The rim may help create a seal between the rim of the flow control cone and the interior surface of the housing during the pump stroke. A conically shaped mesh layer may be formed by the same process except that a rim need not be included.

In addition to a rim, the flow control layer may include a body. The body and the rim may be made from the same material or from different materials. Additionally, the body and the rim may be separate components or integrally formed with one another. When provided as separate components, the body may be formed from an elastomeric polymer or from Mylar® plastic film, and the rim may be an O-ring. The peripheral edge of the flow control layer may be rolled over the O-ring to form the rim. The thickness of the rim may be greater than the thickness of the body. The body may have a thickness ranging from about 0.03 mm to about 0.05 mm, including all values and sub-ranges therein. The rim may have a thickness ranging from about 0.20 mm to about 1.5 mm, including all values and sub-ranges therein. For example, the rim may have a thickness or about 0.20 mm, about 0.30 mm, about 0.40 mm, about 0.50 mm, about 0.60 mm, about 0.70 mm, about 0.80 mm, about 0.90 mm, about 1.0 mm, about 1.1 mm, about 1.2 mm, about 1.3 mm, about 1.4 mm, or about 1.5 mm.

Flexible Diaphragm

In some variations, the linearly reciprocating member of the pumps described herein may include a flexible diaphragm as the valve member. The flexible diaphragm may be contained within the housing. The flexible diaphragm may have a collapsed configuration and an extended configuration, and may linearly reciprocate within the housing. In the collapsed configuration, the flexible diaphragm may have a smaller diameter than when in the extended configuration to allow advancement through the vasculature. Once at the target location in the patient, the flexible diaphragm may be transformed to its extended configuration to move blood from an inlet of the housing, through a body of the housing, to and through an outlet of the housing, and create the pressure needed for pumping blood. The flexible diaphragm may be coupled to a support member, which in turn is coupled to an actuator that linearly reciprocates the flexible diaphragm within the housing. The support member may be an expandable frame that is conically shaped or a tine support, as further described below. Coupling to the expandable frame may be accomplished in any suitable manner, for example, by stitching, suturing, or embroidering, by use of an adhesive, by heat sealing, or by welding. The flexible diaphragm may include a diaphragm body and a rim. In some variations, the flexible diaphragm may comprise an elastomeric polymer. Non-limiting examples of elastomeric polymers include but are not limited to: silicone, polyester, polyurethane elastomers, or a combination thereof. The body and rim of the flexible diaphragm may comprise the same material or different materials. In some instances, the diaphragm body and rim are integrally formed.

The material and/or thickness of the diaphragm body and rim may be selected so that the flexible diaphragm is able to bend and allow blood to flow around it during a fill stroke, but resilient enough to prevent the flexible diaphragm from everting or folding upon itself during a pump stroke. Furthermore, the material and/or thickness of the flexible diaphragm may be sufficiently rigid so that the pressure needed to effect a pump stroke is generated as well as to prevent stretching of the diaphragm body. In one variation, the flexible diaphragm may maintain its shape during the pumping cycle by including a rim thicker than the diaphragm body.

In some variations, thicknesses of the diaphragm body may range from about 0.03 mm to about 0.3 mm, including all values and sub-ranges therein. For example, diaphragm thickness may be about 0.03 mm, about 0.04 mm, about 0.05 mm, about 0.06 mm, about 0.07 mm, about 0.08 mm, about 0.09 mm, about 0.10 mm, about 0.20 mm, or about 0.30 mm. With respect to the rim of the diaphragm, its thickness may range from about 0.20 mm to about 1.5 mm, including all values and sub-ranges therein. For example, the rim thickness may be about 0.20 mm, about 0.30 mm, about 0.40 mm, about 0.50 mm, about 0.60 mm, about 0.70 mm, about 0.80 mm, about 0.90 mm, about 1.0 mm, about 1.1 mm, about 1.2 mm, about 1.3 mm, about 1.4 mm, or about 1.5 mm. In some variations, the rim thickness may range from about 0.5 mm to about 1.0 mm, including all values and sub-ranges therein. The thickness of the rim may be greater than the thickness of the diaphragm body, which may help the flexible diaphragm maintain its shape during the pumping cycle, as mentioned above. A greater rim thickness may also aid in creating a seal between the rim and interior surface of the housing during the pump stroke. However, in some variations, the rim and body may have equal thicknesses. The ratio of the thickness between the diaphragm body and rim may range from about 1:5 about 1:20. The rim of the flexible diaphragm may have a width ranging from about 1.0 mm to about 2.0 mm, including all values and sub-ranges therein. In one variation, the diaphragm body may have a thickness of about 0.05 mm and the rim may have a thickness of about 0.25 mm.

Furthermore, the flexible diaphragm may have any suitable shape or geometry capable of creating a seal between the rim of the diaphragm and the interior surface of the housing during the pump stroke. For example, the flexible diaphragm may have a conical, frustoconical, or hemispherical shape when in the extended configuration. The flexible diaphragm may also comprise a plurality of ribs that may help provide more rigidity to the flexible diaphragm body. In one variation, the flexible diaphragm has a conical shape and a plurality of ribs that aid in maintaining the conical shape during a pump stroke. The plurality of ribs may be integrally formed with the diaphragm body, or they may be separate components coupled to the diaphragm body by, e.g., use of an adhesive, welding, etc. In some variations, the plurality of ribs may radiate from a center portion of the diaphragm body to the rim. The plurality of ribs may have a rib angle between a longitudinal axis of a rib of the plurality of ribs and an axis perpendicular to the actuator that ranges from about 30 degrees to about 60 degrees, including all values and sub-ranges therein. For example, the rib angle may be about 30 degrees, about 35 degrees, about 40 degrees, about 45 degrees, about 50 degrees, about 55 degrees, or about 60 degrees. The plurality of ribs may be equally spaced from one another. In some variations, the plurality of ribs may have unequal spacing from one another.

Actuator/Controller

The pumps described herein may include an actuator coupled to the valve member, usually via a support member. The valve member may be a flexible diaphragm or a valve cone. The actuator may be generally configured to linearly reciprocate the flexible diaphragm or valve cone within the housing to generate a fill stroke and a pump stroke of a pumping cycle. Exemplary actuators may include without limitation, a cable, a wire, a rod, or other actuator having the flexibility to track over a guidewire and navigate the vasculature, as well as the stiffness needed to reciprocate the flexible diaphragm during the pump and fill strokes. The linear reciprocating movement of the actuator may be generated by a linear motor drive and linear motor controller. Although the linear motor is usually situated external to the patient, in some variations, the linear motor may be implanted within the patient, e.g., in a subcutaneous pocket, or provided as part of the pump placed within the heart or vasculature of the patient.

The linear motor controller may regulate various parameters of the pumping cycle. For example, the linear motor controller may regulate the speed of linear reciprocation of the actuator and flexible diaphragm, and the length of the pump and fill strokes. In some variations, the adjustment or control of pump parameters may be accomplished manually, e.g., by one or more control features provided on an external console. In other variations, pump parameters may be adjusted automatically, e.g., using a closed loop system. The closed loop system may comprise a processor and instructions stored in memory of the processor. During operation of the pump, the processor may store and/or process data from the pump and/or patient, and may execute instructions from memory to automatically adjust pump parameters based on data received from one or more sensors provided with the pump.

Non-limiting examples of sensors for controlling pump parameters include pressure sensors, flow sensors, temperature sensors, heart rate sensors, and heart rhythm sensors. The pressure sensors may be placed in various pump locations. In some variations, one or more pressure sensors may be mounted in or on a blood flow inlet or inlet/inflow tubing, and one or more pressure sensors may be mounted in or on a blood flow outlet, outlet/outflow tubing, or skirt of the pump. In other variations, two pressure sensors may be mounted in or on the inlets and outlets for redundancy in case one inlet and/or outlet pressure sensor fails. In further variations, one or more pressure sensors may be mounted near a blood flow inlet or inlet/inflow tubing, and one or more pressure sensors may be mounted near a blood flow outlet, outlet/outflow tubing, or skirt of the pump. The pressure sensors may be communicatively coupled to the controller such that the controller may receive measurements from the pressure sensors and may utilize those measurements to modify pump parameters, as stated above. For example, in some variations, the controller may be configured to have predetermined high blood pressure set points, low blood pressure set points and/or a predetermined target blood pressure range. The controller may be further configured to compare the measurements received from one or more of the pressure sensors to the high blood pressure set points, low blood pressure set points, and/or the predetermined desired blood pressure range and to modify one or more pump parameters (e.g., speed of reciprocation) accordingly. For example, when measurements from the pressure sensors indicate that a patient's measured blood pressure has dropped below the low set point and/or is below the desired range, the controller may increase the speed of the linear reciprocation. When measurements from the pressure sensors indicate that a patient's measured blood pressure has risen above the high blood pressure set point and/or is above the desired range, the controller may decrease the speed of the linear reciprocation to thereby reduce flow and return blood pressure back below the high set point and/or within the target range.

Tines

Some variations of the pumps described herein may also comprise a tine support as the support member. The tine support may comprise a base and a plurality of tines configured to support the flexible diaphragm in the extended configuration during the pump stroke. In other variations, as described further below in FIGS. 5-7, the tine support may be coupled to the flexible diaphragm. The plurality of tines may be flexible and/or resilient, and may have an expanded configuration and a compressed configuration. In the compressed configuration, the plurality of tines may have a smaller diameter than when in the extended configuration to allow advancement through the vasculature. Once at the target location in the patient, the plurality of tines may be expanded to a larger diameter. Furthermore, the plurality of tines may have an expanded configuration during the pump stroke of a linear pumping cycle, and a compressed configuration or partially compressed configuration during the fill stroke. The plurality of tines may be coupled to the actuator. In one variation, each of the plurality of tines may extend from a common hub or base to a free end. The hub may be configured to couple to the actuator. Furthermore, the free ends of the plurality of tines may radiate or flex outwardly when the plurality of tines move from the compressed to the expanded configuration.

The number of tines included in the plurality of tines may range from about two to about eight. For example, the plurality of tines may include two (2) tines, three (3) tines, four (4) tines, five (5) tines, six (6) tines, seven (7) tines, or eight (8) tines. In one variation, the plurality of tines includes six (6) tines. The plurality of tines may be equally spaced or unequally spaced from one another. With respect to materials, the plurality of tines may be made from a metal such as stainless steel, titanium, or alloys thereof, or a biocompatible polymer such as a fluoropolymer, a polyamide, polyetheretherketone (PEEK), a polyimide, a polyolefin, a polyurethane, or combinations thereof.

In one variation, the plurality of tines may comprise metal strips. The metal strips may extend from a common base at one end. At the other end, each tine of the plurality of tines has a free end. The free ends may be attached to a barrel, e.g., a short cylinder, by welding, soldering, or gluing. The barrels may provide further supportive area for the flexible diaphragm to rest against during a pump stroke to help prevent movement of the flexible diaphragm between the tines during the pump stroke. In one variation, the length of each barrel is about 1.0 mm. The tines may be made from a metal cylinder that is laser cut to form the strips.

Instead of strips, the plurality of tines may comprise a plurality of flexible first wires. Any suitable number of first wires may be employed. For example, four (4) wires, six (6) wires, eight (8) wires, ten (10) wires, or 12 (twelve) wires may be used. A plurality of holes corresponding to the number of first wires may be drilled into a base so that one end of the wires may be inserted into the holes. At the other end of the wires (free ends), a barrel may be attached in the same manner described above. The barrels may include a central hole through which a second wire is threaded. After threading through all the barrels, the ends of the second wire may be joined by soldering, welding, gluing, and the like. The second wire may be made from various materials, including but not limited to, stainless steel, spring steel (piano wire), or nitinol. In some variations, each tine of the plurality of tines may be comprised of two wires attached to the same barrel at their free ends. Thus, when the plurality of tines includes 6 (six) tines, the number of wires would be twelve (12). The second wire may provide additional flexible diaphragm support to that provided by the barrels during a pump stroke so that movement of the flexible diaphragm between the tines during the pump stroke is prevented or minimized.

Exemplary Variations

An exemplary pump is shown in FIG. 1. As shown there, pump 10 includes an elongated outer sheath 11 having an interior end 12 supporting a bearing 13. An expandable housing 25 (better seen in FIG. 3) is received within the interior of outer sheath 11 and holds bearing 13 in a fixed attachment. An inner sheath 16 extends through the interior of outer sheath 11 from bearing 13. Tine support 15 having a plurality of tines 20 for supporting a flexible diaphragm 30 is disposed within inner sheath 16 in a collapsed configuration. An actuator (drive cable) 40 is coupled to tine support 15 by a fixed attachment at one end and extends through the interior of inner sheath 16 to attach to linear motor 19 within linear motor drive 18 at its other end.

Figure 4:
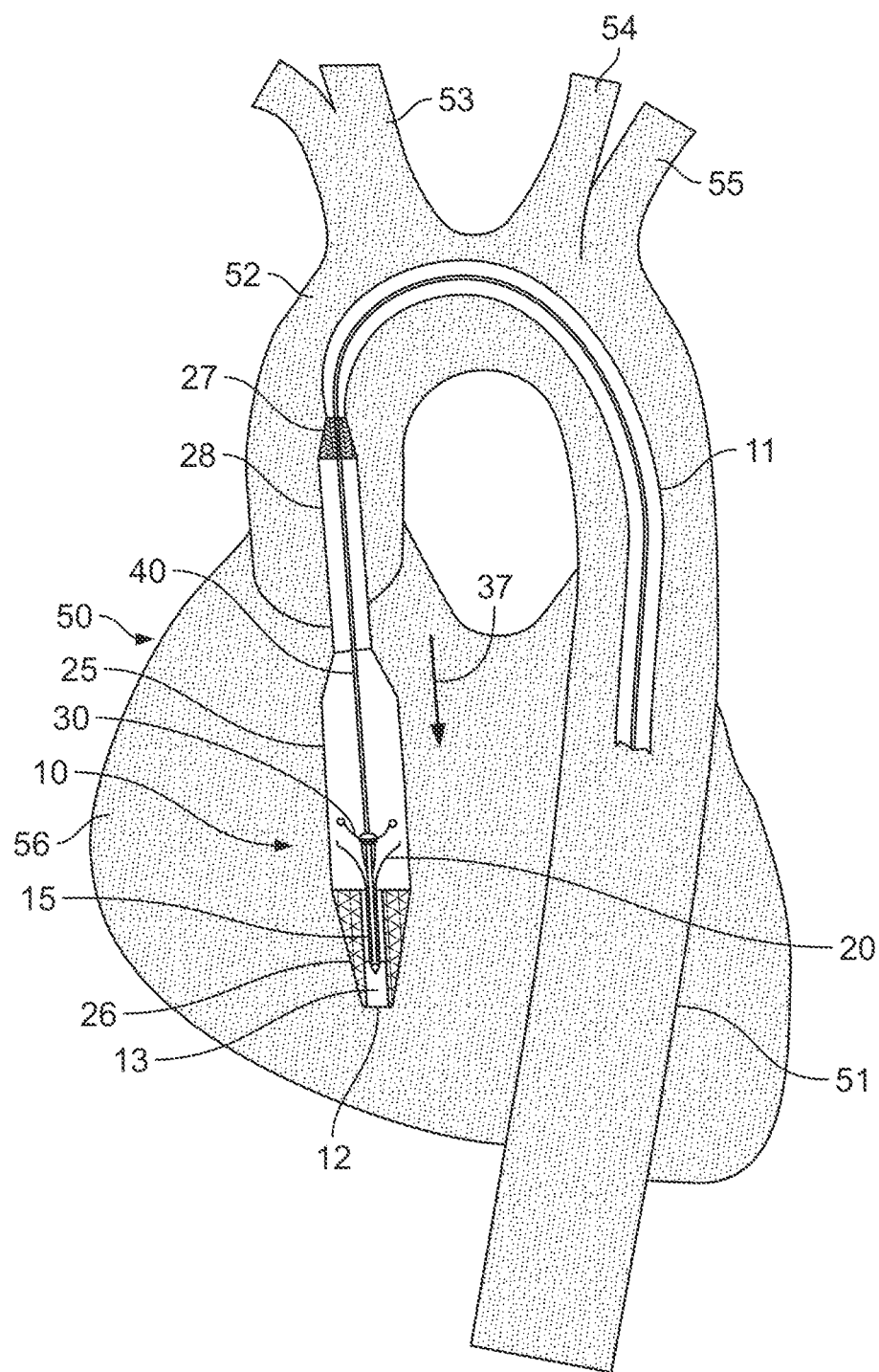
FIG. 4 illustrates the filling stroke of the pump of FIG. 2.
Figure 5:
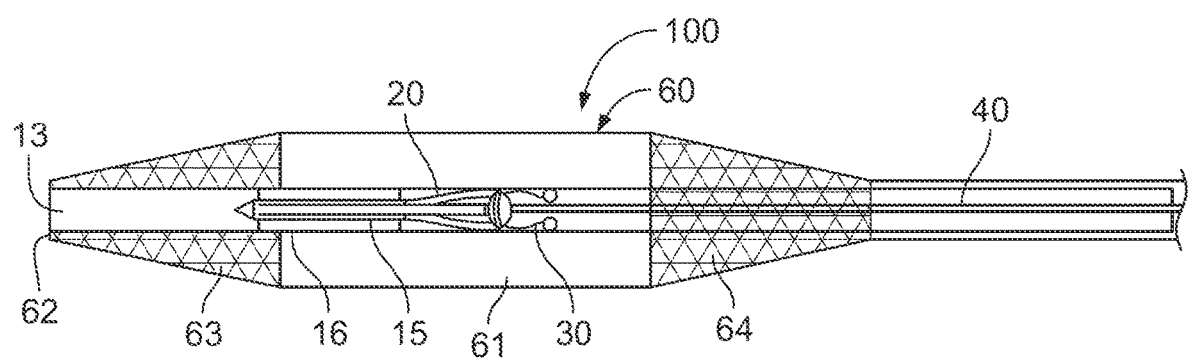
FIG. 5 depicts an enlarged cross-sectional view of the pump of FIG. 1 prior to deployment in a heart.
Figure 6:
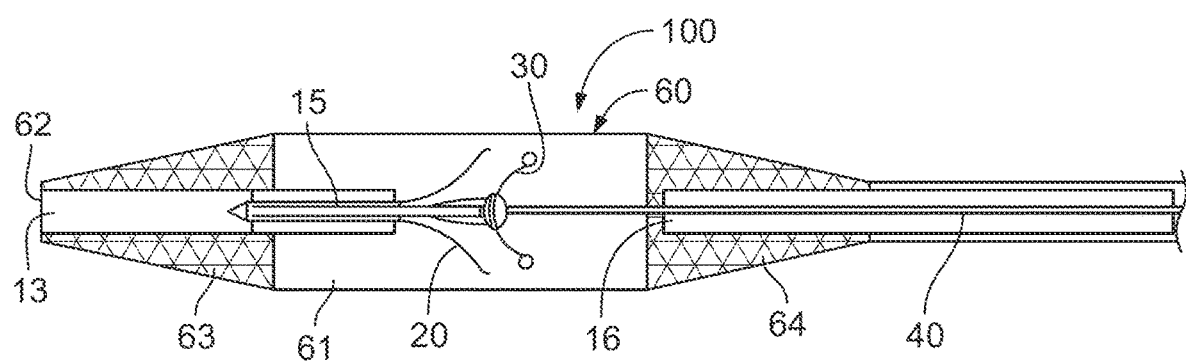
FIG. 6 depicts an enlarged cross-sectional view of the pump of FIG. 1 at an intermediate point during its configuration for pumping operation.
Figure 7:
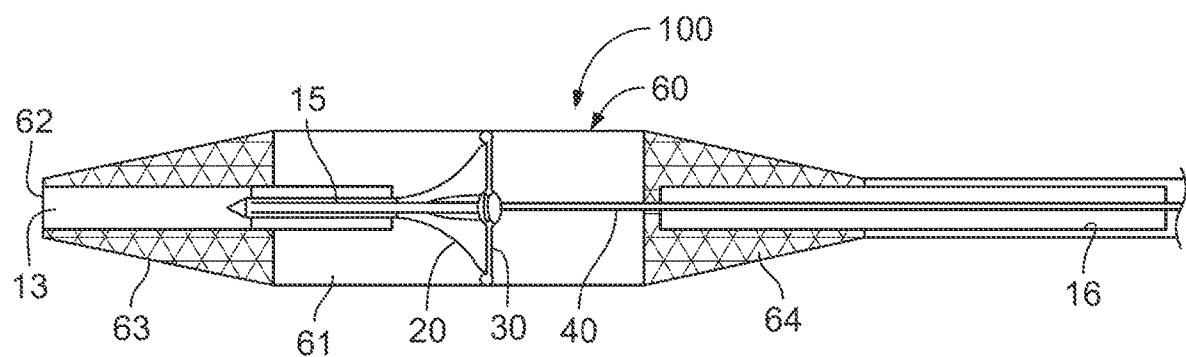
FIG. 7 depicts an enlarged cross-sectional view of the pump of FIG. 1 at the completion of its configuration for pumping operation.

Referring to FIGS. 5, 6 and 7, another variation of the pump is illustrated. In these figures, pump 100 is substantially identical to pump 10 both in structure and function with the difference being found in the configuration of the expandable housings. In comparison to FIGS. 3 and 4, it will be noted that pump 10 utilizes an expandable housing 25 having a cannula or an extended portion 28 extending therefrom. Turning to FIG. 5, it will be noted that pump 100 utilizes an expandable housing 60 that does not have a cannula or extended portion 28. Apart from this difference in structure of the expandable housings, pumps 10 and 100 are substantially identical.

More specifically, FIG. 5 sets forth a section view of the pulsatile pump portion (expandable housing and flexible diaphragm) of pump 100. FIG. 5 shows the expandable housing 60 in its collapsed configuration. The expandable housing 60 may be advanced from within an outer sheath 11 (shown in FIG. 4). Expandable housing 60 includes an inlet (scaffold portion) 63 proximate end 62, which in turn supports a bearing 13 in a fixed attachment. Expandable housing 60 further includes an outlet (scaffold portion) 64 and a chamber 61 within expandable housing 60. The chamber 61 may be formed by overmolding a portion of the scaffold of expandable housing 60 with a polymer layer or coupling a fabric layer to the scaffold, as previously described. Pump 100 further includes an inner sheath 16 which extends through outlet 64 and chamber 61 to the interior end of bearing 13. Tine support 15 is received within inner sheath 16 and includes a plurality of tines 20. A drive cable 40 extends through inner sheath 16 and is coupled to tine support 15. A flexible diaphragm 30 is also coupled to tine support 15.

In the configuration shown in FIG. 5, pump 100 has initiated the expansion of expandable housing 60 while tine support 15 remains captivated within inner sheath 16 in the compressed configuration. Thus, the next step in configuring pump 100 for operation requires withdrawing inner sheath 16 to allow the plurality of tines 20 to expand and assume their operational expanded configuration.

FIG. 6 sets forth a section view of the pulsatile pump portion of pump 100. As mentioned above, FIG. 6 shows pump 100 at a point intermediate between the compacted configuration of FIG. 5 and the operational configuration of FIG. 7. Pump 100 includes an expandable housing 60. Expandable housing 60 includes an inlet 63 proximate end 62, which in turn supports a bearing 13 in a fixed attachment. Expandable housing 60 further includes an outlet 64 and a chamber 61. pump 100 further includes an inner sheath 16 which has been withdrawn to a point within outlet 64 thereby releasing tines 20 and diaphragm 30 from the captivity of inner sheath 16. Expandable housing 60 further includes a chamber 61 and an end 62. Tine support 15 is received within inner sheath 16 and includes a plurality of tines 20. A drive cable 40 extends through inner sheath 16 and outer sheath 11 and is coupled to tine support 15. A flexible diaphragm 30 is also coupled to tine support 15.

In the configuration shown in FIG. 6, pump 100 has initiated the expansion of expandable housing 60 and release of tine support 15 from inner sheath 16. Thus, the next step in configuring pump 100 for operation requires allowing tines 20 of tine support 15 and diaphragm 30 to expand and assume their operational configurations.

FIG. 7 sets forth a section view of the pulsatile pump portion of pump 100. As mentioned above, FIG. 6 shows pump 100 in its operational configuration. Expandable housing 60 includes an inlet 63 proximate end 62, which in turn supports a bearing 13 in a fixed attachment. Expandable housing 60 further includes a mesh portion 64 and a chamber 61. Pump 100 further includes an inner sheath 16 which has been withdrawn to a point within outlet 64 thereby releasing tines 20 and diaphragm 30 from the captivity of inner sheath 16. Expandable housing 60 further includes a chamber 61 and an end 62. Tine support 15 extends partially into bearing 13. Tine support 15 includes a plurality of tines 20 that have expanded to the position shown. A drive cable 40 extends through inner sheath 16 and outer sheath 11 and is coupled to tine support 15. Flexible diaphragm 30 is also coupled to tine support 15 and has expanded to its full extended configuration overlapping the outer ends of tines 20.

In the configuration shown in FIG. 7, pump 100 has completed the expansion of expandable housing 60 and released tine support 15 from inner sheath 16 allowing tines 20 and diaphragm 30 to assume their fully extended positions. Thus, pump 100 is fully configured for operation.

Figure 10A:
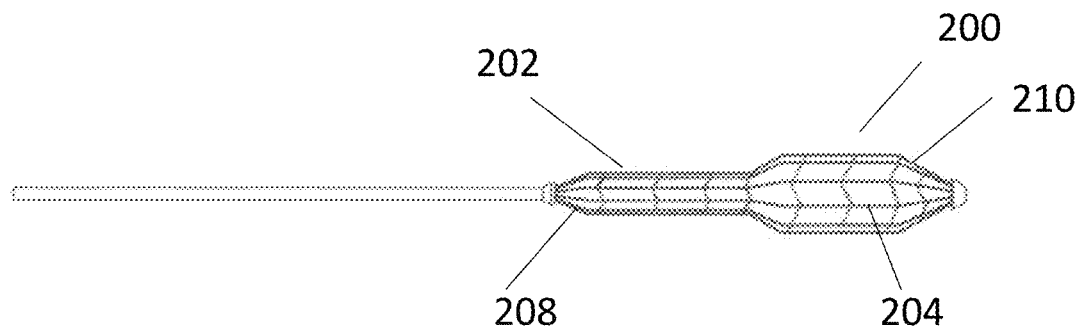
FIGS. 10A-10C depict side views of an exemplary housing comprising a scaffold and blocking layer. The scaffold is shown in FIG. 10A and the blocking layer in FIG. 10B.
Figure 10B:
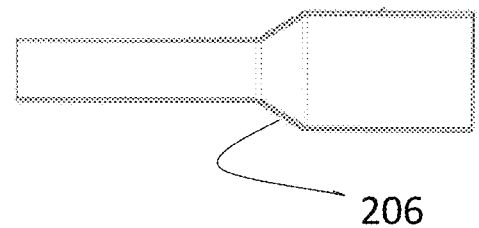
Figure 10C:
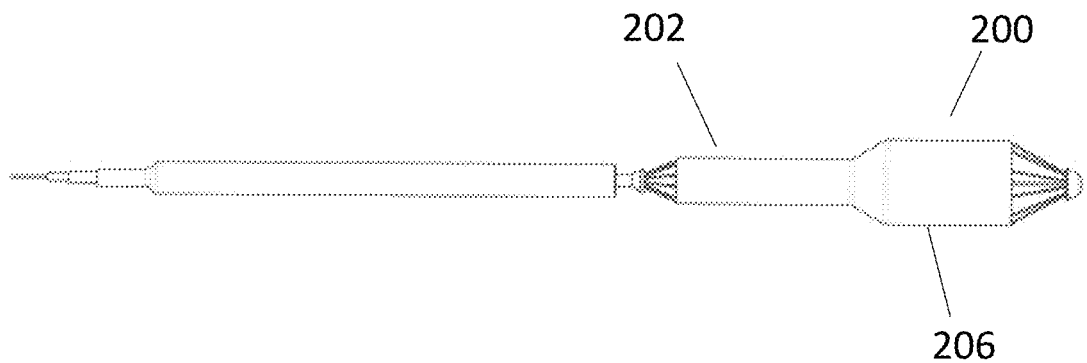

In some variations, the pumps for assisting blood circulation include an expandable housing as illustrated in FIGS. 10A to 10C. Referring to FIG. 10A, expandable housing 200 has a cannula 202 extending therefrom. The cannula 202 may have a smaller diameter than the expandable housing 200, which may be useful when the cannula is to traverse the aortic valve. Expandable housing 200 may comprise a scaffold 204, which, in some variations, may be an expandable stent. Scaffold 204 may include a tapered proximal end 208 and a tapered distal end 210, although, it need not. The distal end 210 may function as an inlet for blood into the expandable housing 200 and the proximal end 208 may function as an outlet for blood exiting the expandable housing 200. In order to block blood from flowing through the stent openings and provide a smooth surface upon which the flexible diaphragm can reciprocate, the expandable housing 200 may comprise a layer 206 coupled to and/or covering the scaffold (e.g., stent) 204. FIG. 10B depicts a polymer layer 206 that may be overmolded on or otherwise attached to the scaffold 204. The polymer layer 206 may be overmolded on the scaffold 204 such that the scaffold 204 is embedded within or otherwise fully surrounded by the polymer layer 206. FIG. 10C shows the expandable housing 200 and cannula 202 with the polymer layer 206 coupled to the scaffold 204.

Figure 11:
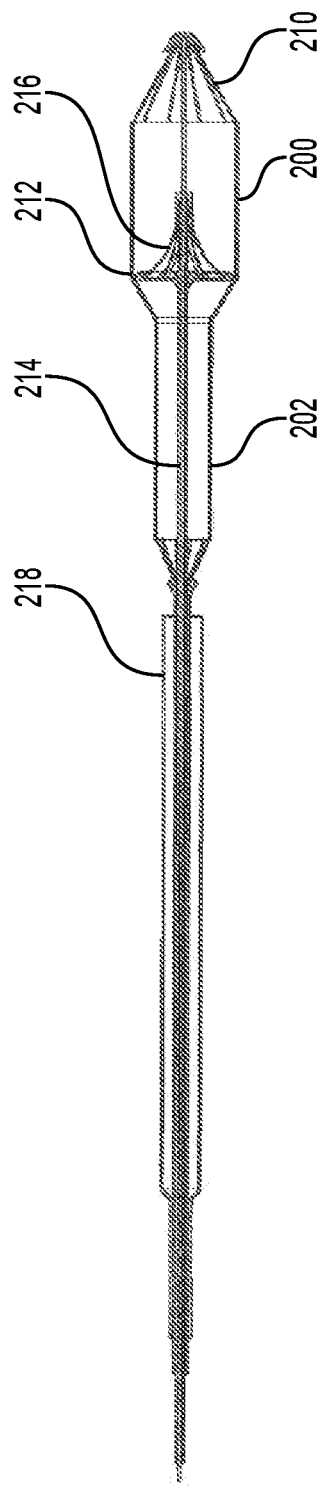
FIG. 11 depicts a perspective view of an exemplary pump including the housing of FIG. 10C and a flexible diaphragm supported by a plurality of tines.

The expandable housing in FIG. 10C may include a flexible diaphragm, which may be, in some variations, supported by a plurality of tines, as shown in FIG. 11. Referring to FIG. 11, flexible diaphragm 212 may be disposed within a chamber formed in the body of the expandable housing 200. and the flexible diaphragm 212 may have a collapsed configuration and an expanded configuration (as depicted in FIG. 11). Flexible diaphragm 212 may be coupled to actuator 214 such that linear movement of the actuator 214 results in corresponding linear movement of the diaphragm 212. A plurality of tines 216, which may help support the flexible diaphragm 214 against blood pressure during the pump stroke, are also shown in their expanded configuration. The expandable housing 200, flexible diaphragm 212, and/or tines 216 may be configured to self-expand, such that expansion of the expandable housing 200, flexible diaphragm 212, and tines 216 may be achieved by relative motion between the expandable housing 200 and a flexible outer sheath 218 that may be constraining the expandable housing 200, flexible diaphragm 212 and/or tines during advancement to the desired position in the body (e.g., retraction of the outer sheath 218 and/or advancement of expandable housing 200 relative to outer sheath 218).

Figure 12A:
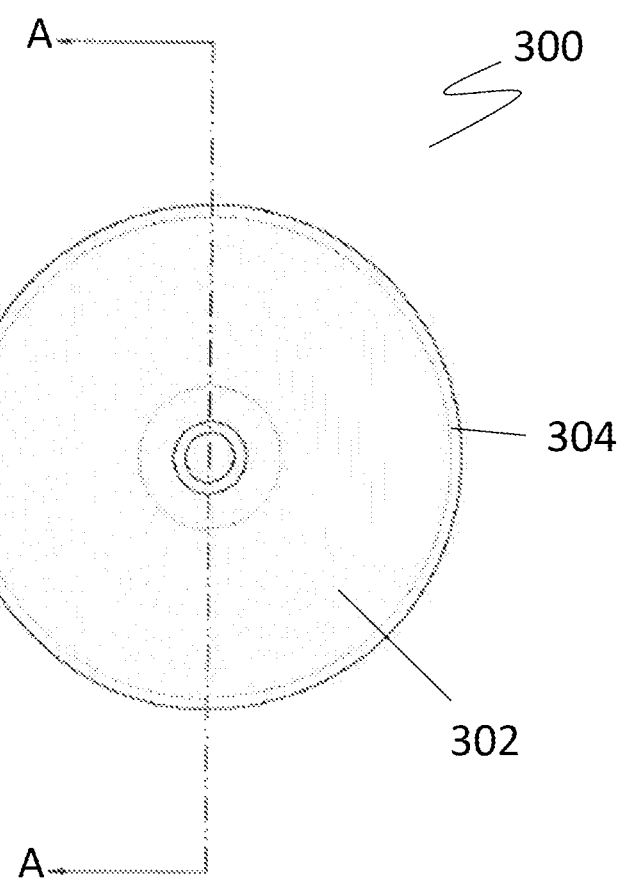
FIGS. 12A and 12B depict an enlarged view of a flexible diaphragm according to one variation.

In general, the flexible diaphragm contained within the expandable housing moves blood from an inlet of the housing, through the chamber in the body of the expandable housing, to and through an outlet of the housing, and creates the pressure for pumping blood. As shown in FIG. 12A, the flexible diaphragm 300 in its extended configuration includes a diaphragm body 302 and a rim 304 about the periphery of the body 302. The body 302 and rim 304 of the flexible diaphragm 300 are integrally formed. However, in other variations, they may be formed separately and coupled to one another.

Figure 12B:
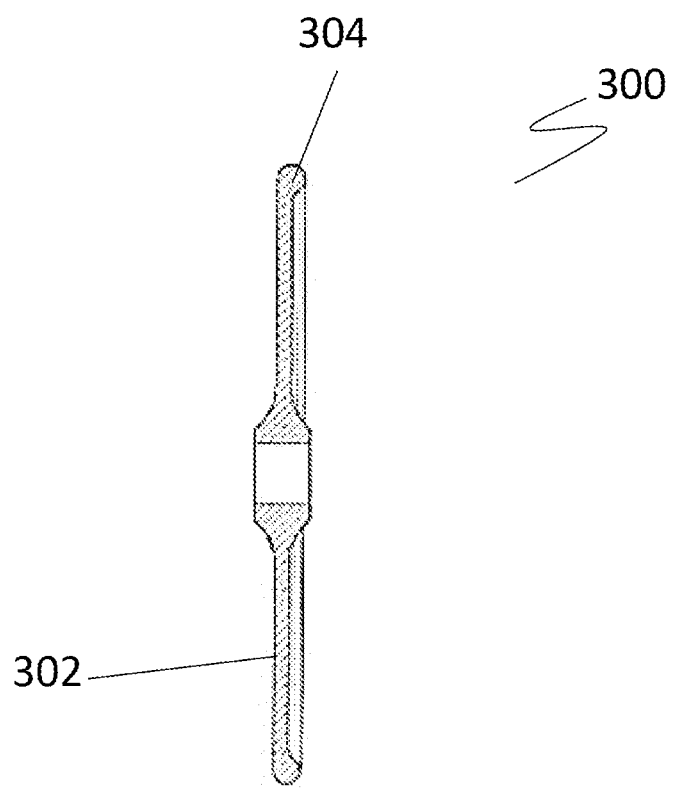

In some variations, the diaphragm body 302 and the rim 304 may have different thicknesses. For example, in some variations, the thickness of the rim 304 may be greater than the thickness of the diaphragm body 302, as shown in the cross-section view provided in FIG. 12B. The smaller thickness of the diaphragm body 302 may allow the flexible diaphragm to be in its collapsed configuration during the fill stroke or a portion thereof, and the extended configuration during the pump stroke of a pumping cycle. The greater rim thickness may provide the periphery of the diaphragm 300 with greater rigidity relative to the diaphragm body 302 and may aid in creating a seal between the rim 304 and interior surface of the expandable housing during the pump stroke.

Some variations of the pump may include a tine support comprising a base and a plurality of tines coupled to the actuator that support the flexible diaphragm in the extended configuration during the pump stroke. For example, as shown in FIGS. 13A to 13C, tine support 401 includes a base 404 and a plurality of tines 400. The plurality of tines 400 may comprise six (6) pliable metal strips 402 having an expanded configuration (as shown in the FIG. 13A) and a compressed configuration (see FIG. 5). The metal strips 402 may have a compressed configuration during advancement of the expandable housing within the vasculature to a target location, and may expand radially outward to an expanded configuration at the target location. Although shown as having a rectangular cross-sectional shape, the plurality of tines 400 may have any suitable shape or geometry, e.g., circular, square, triangular, ovoid, etc. The metal strips 402 may extend from a common hub or base 404 at one end, and may have free ends 406 at the other end. As shown in the cross-section view of FIG. 13B, the base 404 may include a bore 408 configured to couple the plurality tines to an actuator. Although shown as including six (6) metal strips 402, more or less strips may be utilized. The metal strips 402 may be equally spaced from one another, as shown in FIG. 13C. However, in some variations, the metal strips 402 may be unequally spaced from one another. Also shown in FIGS. 13A to 13C are barrels 412, which are short cylinders attached to the free ends 406 of the metal strips 402. The free ends 406 may be attached to a barrel 412 using any suitable means, such as, for example, by welding, soldering, or gluing. The barrels 412 may provide further supportive area for the flexible diaphragm to rest against during a pump stroke to help prevent movement of the flexible diaphragm between the tines during the pump stroke.

In some variations, the plurality of tines 500 may comprise a plurality of flexible first wires 502, as illustrated in FIGS. 14A to 14C. Although each tine of the plurality of tines in the figure is shown to include two first wires 502, they may include one wire or more than two wires. A plurality of holes (not shown) corresponding to the number of first wires 502 may be formed (e.g., drilled) in a base 504 of the tine support 501 so that one end of the wires may be inserted into the holes. At the other end of the wires (free ends 506), a barrel 508 is attached in the same manner described above. More specifically, in FIGS. 14A to 14C, pairs of first wires 502 are attached to the same barrel at their free ends 506 to form one tine of the plurality of tines. Accordingly, six (6) tines are formed when pairing the twelve (12) first wires. The barrels 508 may each include a central hole 510 through which a second wire 512 may be threaded. After threading through all the barrels 508, the ends of the second wire 512 may be joined by soldering, welding, gluing, and/or the like. The second wire may provide additional flexible diaphragm support to that provided by the barrels during a pump stroke so that movement of the flexible diaphragm between the tines during the pump stroke may be prevented or minimized. As shown in the cross-section view of FIG. 14B, the base 504 may include a bore 514 configured for coupling to an actuator. The first wires 502 may be equally spaced from one another, as shown in FIG. 14C. However, the first wires 502 may also be configured to be unequally spaced from one another.

Figure 15:
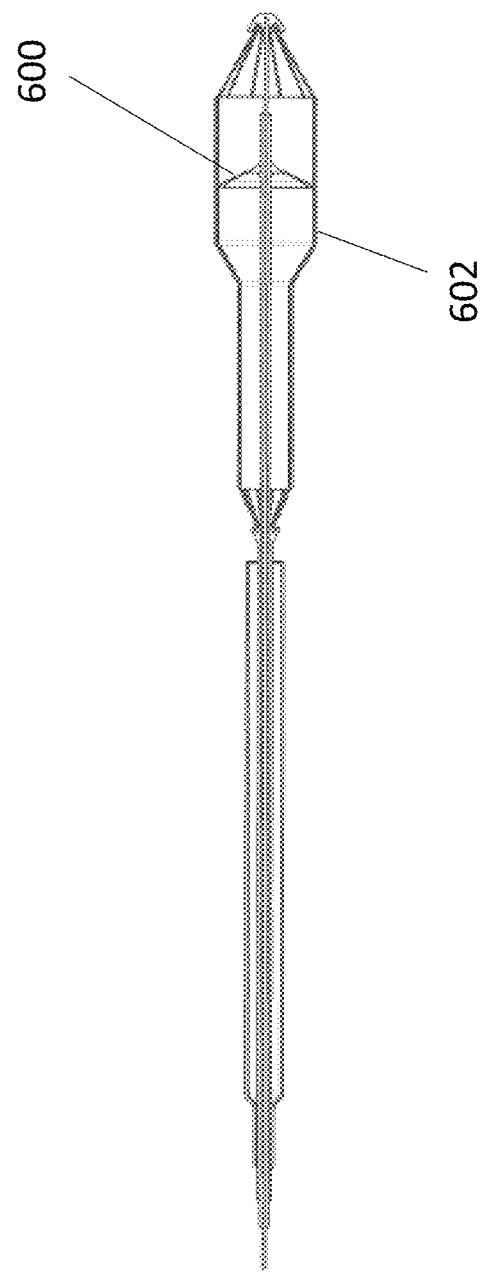
FIG. 15 depicts a perspective view of another exemplary pump including a conical shaped flexible diaphragm.
Figure 16A:
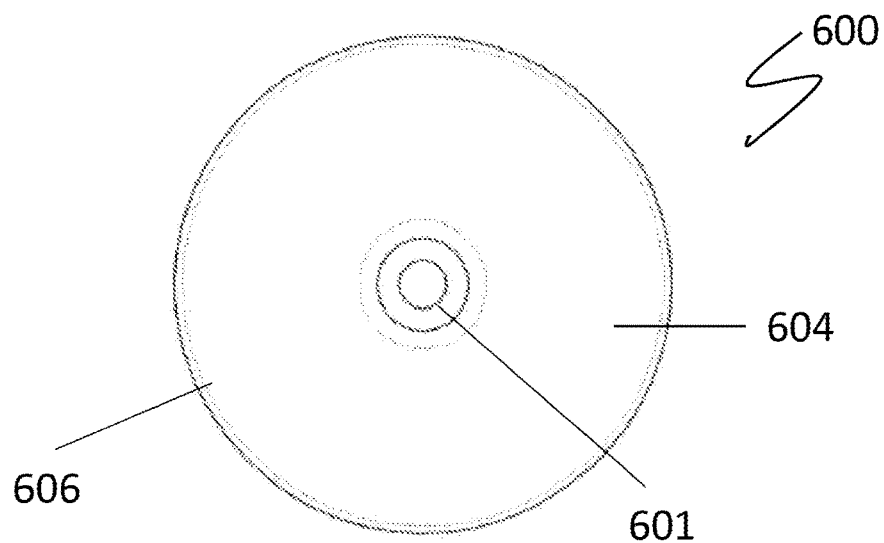
FIGS. 16A-16C depicts enlarged views of the conical shaped flexible diaphragm of FIG. 15.
Figure 16B:
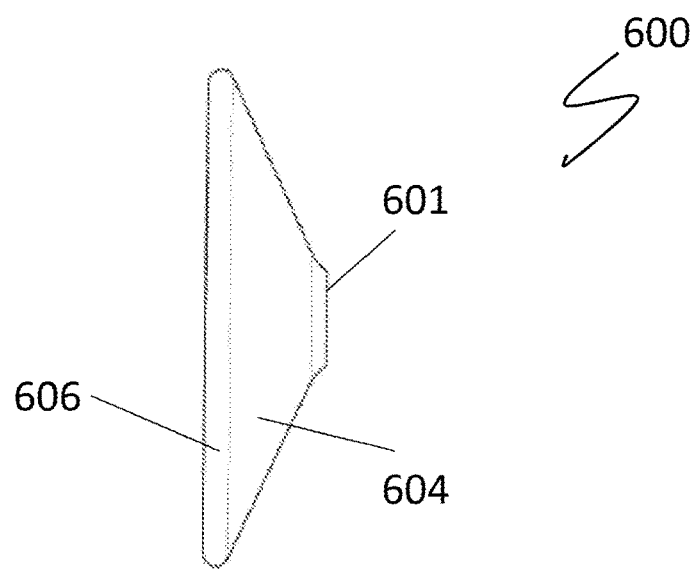

Other pump variations may not include a plurality of tines supporting the flexible diaphragm. For example, as shown in FIG. 15, a flexible cone shaped diaphragm 600 is disposed within expandable housing 602. The flexible diaphragm 600 may have a compressed configuration and an extended configuration, and may have a conical shape when in the extended configuration. As shown in FIGS. 16A (end view) and 16B (side view), the flexible diaphragm 600 may include a diaphragm body 604 and a rim 606 about the periphery of the body 602. As depicted FIGS. 16A-16B, the body 604 and rim 606 of the flexible diaphragm 600 may be integrally formed and may be formed from the same material. However, in other variations, they may be separate components and/or may comprise different materials.

Figure 17:
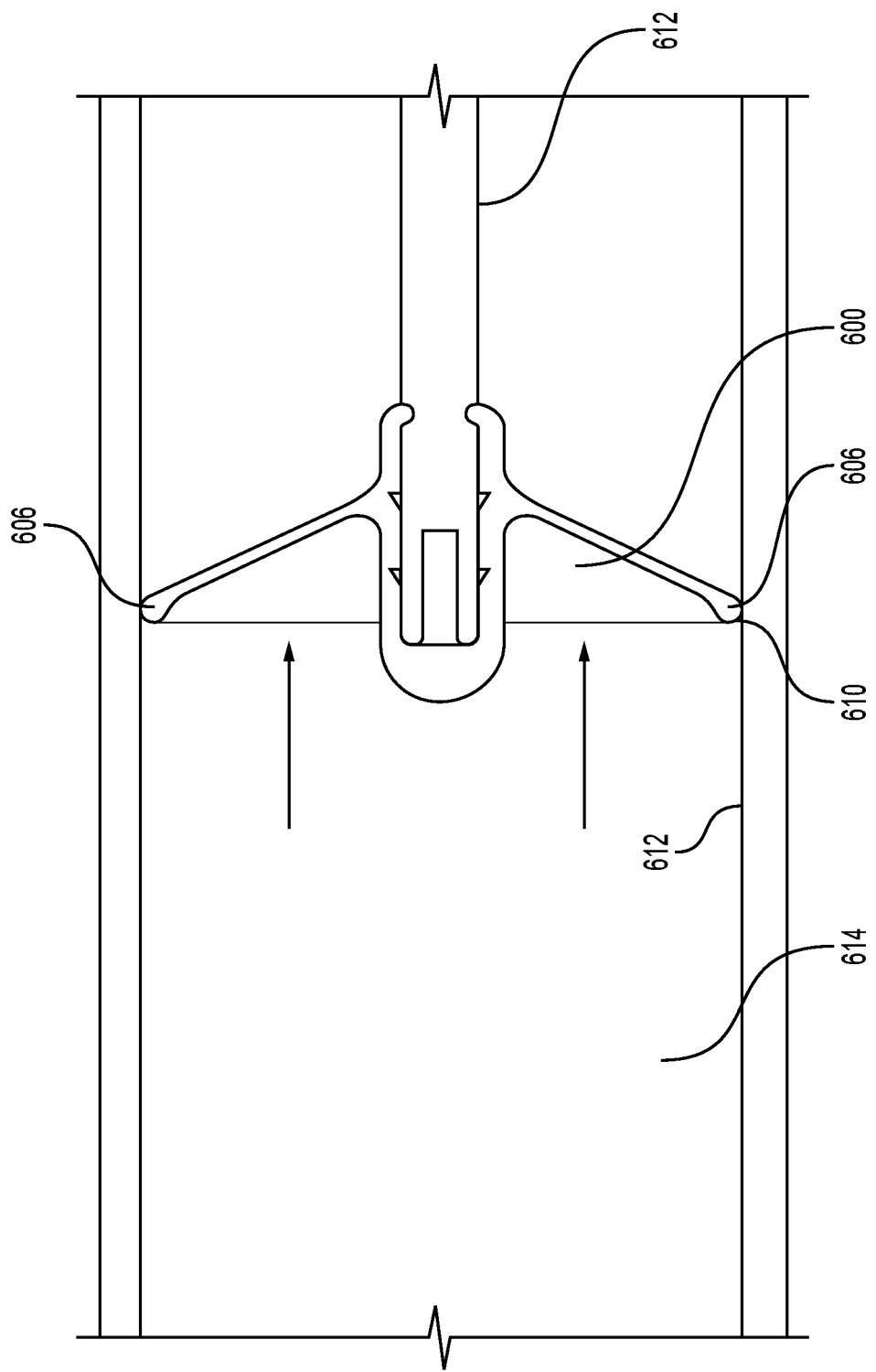
FIG. 17 illustrates seal formation between an exemplary conical shaped flexible diaphragm and an interior surface of a housing.

In some variations, the body 604 and the rib 606 may have the same thickness, while in other variations, the thicknesses of the body 604 and the rim 606 may differ. For example, in some instances, it may be advantageous to utilize a diaphragm with a rim 606 that has a greater thickness than the body 604. Turning to FIG. 17, shown there is an enlarged cross-sectional view of diaphragm 600 in an extended configuration, coupled to actuator 612 and positioned within the chamber of the body of expandable housing 614. Rim 606 contacts interior surface 612 of the expandable housing 614 such that a seal 610 may be formed between the expandable housing 614 and the diaphragm 600. As can also be seen in FIG. 17, rim 606 of diaphragm 600 has a greater thickness than diaphragm body 604. The greater thickness of rim 606 may aid in creating the seal 610 between the rim 606 and interior surface 612 of the expandable housing during the pump stroke, while still allowing for diaphragm body 606 to have the flexibility necessary for collapse during the fill stroke. In this variation, the conical shape of the diaphragm helps to seal the diaphragm against the interior surface 612 and also prevent eversion of the diaphragm when pressure from blood flow (in the direction of arrows) pushes against it.

Figure 16C:
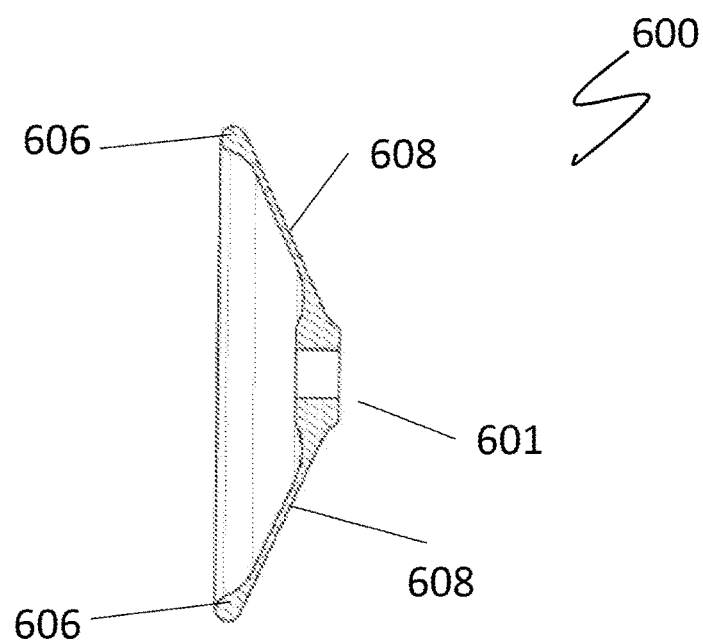

In some variations, the flexible diaphragm may comprise one or more (e.g., a plurality, two, three, four, five, six or more) ribs. Referring to the cross-sectional view provided in FIG. 16C, a plurality of ribs 608 may extend from a center portion 601 of the diaphragm body 604 to the rim 606. The plurality of ribs 608 may be employed to maintain the conical shape of the diaphragm body 604 during a pump stroke. The plurality of ribs 608 may have a rib angle between the longitudinal axis of each rib and an axis perpendicular to the actuator of about 60 degrees. Although the plurality of ribs 608 are shown as equally spaced from one another, in some instances they may be spaced unequally from one another.

Instead of a flexible diaphragm, the pumps may include a valve cone as the linearly reciprocating valve member. In one variation, as illustrated in FIGS. 25A to 25C, the valve cone 1200 may include an expandable frame 1202, a mesh cone 1204, and a flow control cone 1206. Flow control cone 1206 includes a plurality of arc shaped flaps 1212. Other flap shapes may also be used. Additionally, although the expandable frame 1202, mesh cone 1204, and flow control cone 1206 are shown as conically shaped, they may be formed to have a different shape. Expandable frame 1202 may be a stent-like structure having an expanded configuration at one end and a collapsed configuration. In the expanded cone shape shown in the figures, the expandable frame 1202 contains the mesh cone 1204 and the flow control cone 1204 within the cone 1208 of the frame 1202. The flow control valve 1200 may be generally configured such that the mesh cone 1204 sits between the flow control cone 1206 and the expandable frame 1202. In this configuration, the plurality of flaps 1212 open in the direction of arrow A when blood is pulled through the mesh cone into the expandable housing during the fill stroke, and close when blood is moved out of the expandable housing in the direction of arrow B during the pump stroke, as illustrated in FIG. 25B. The mesh cone 1204 may be disposed between the flow control cone 1206 and the expandable frame 1202 to provide support to the flaps 1212 of the flow control cone 1206 such that when pressure against the flaps 1212 is applied during the pump stroke, the flaps 1212 are not pushed or bent through the openings 1201 in the expandable frame 1202. Thus, the mesh cone 1204 may help maintain the flaps 1212 in the closed configuration during the pump stroke when blood is moved out of the housing via the housing outlet. However, during the fill stroke, the mesh cone 1204 permits blood to flow from the housing inlet through the holes in the mesh and then through the flaps 1212, transitioning them to their open configuration so that blood may move to the outlet side of the valve cone. The mesh cone 1204 and flow control cone 1206 may be stitched to the expandable frame 1202 at multiple attachment points 1210, as shown in FIG. 25C. Other mechanisms of attaching the material layers to the expandable frame may also be employed.

Figure 26A:
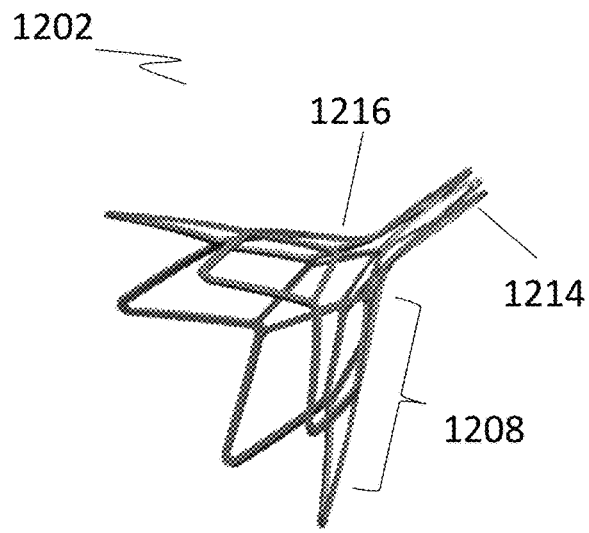
FIGS. 26A-26C depict the expandable frame shown in FIGS. 25A and 25B.
Figure 26B:
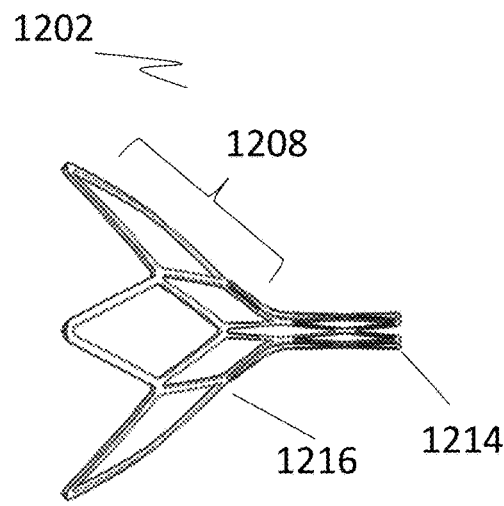
Figure 26C:
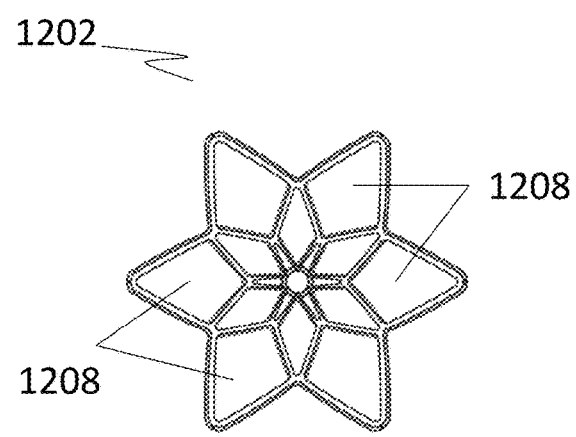

The expandable frame 1202 is shown separately from the rest of the valve cone depicted in FIGS. 26A to 26C. FIG. 26A provides a perspective view of the expandable frame 1202, FIG. 26B provides a side view of the frame 1202, and FIG. 26C provides a top view of the frame 1202. As shown in the figures, expandable frame 1202 may include a first end 1214 and a second end 1216. The first end 1214 may be coupled to an actuator for reciprocating the valve cone back and forth within the housing. The second end 1216 is generally expandable to form a shaped end, for example, cone shape 1208. The expandable frame 1202 may comprise a plurality of cells 1218, which may be diamond shaped. However, the cell shape is not so limited, and they may have any suitable shape. In addition, the cells may have any suitable size. In one variation, the cells may be sized smaller than the flaps in the flow control cone so that the flaps are not pushed through the cells during the pump stroke.

Figure 27A:
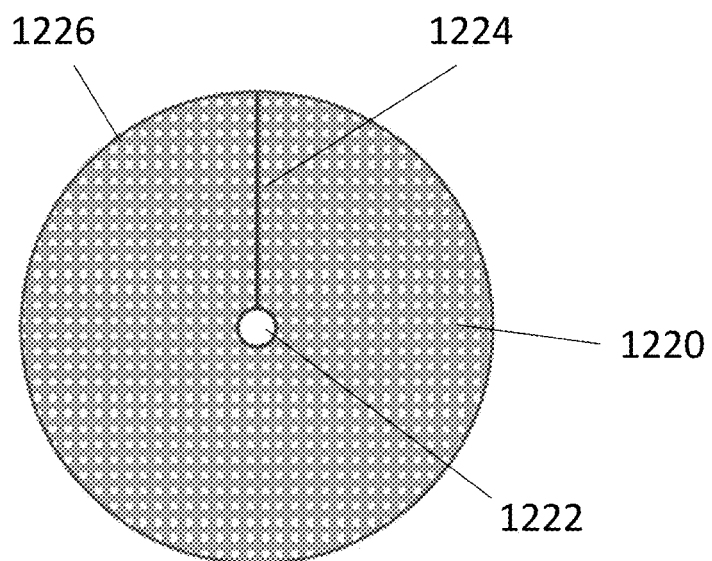
FIGS. 27A and 27B depict the mesh cone of FIGS. 25A to 25C.
Figure 27B:
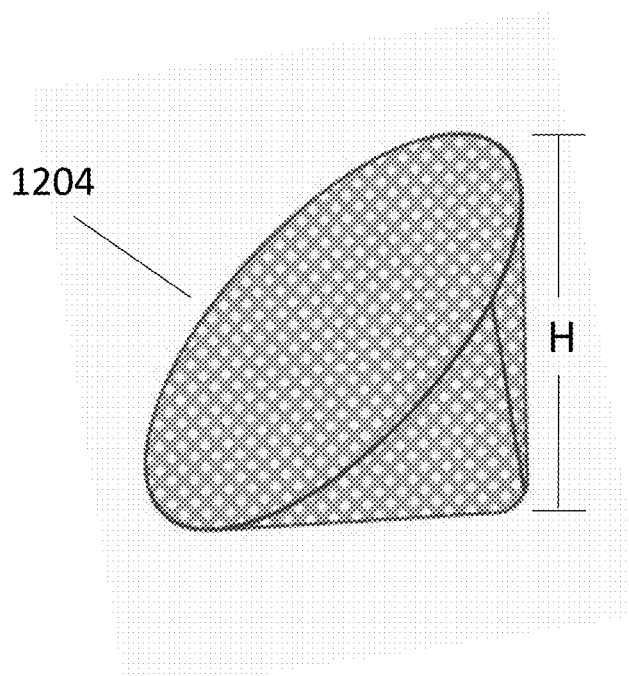

In FIGS. 27A and 27B, the mesh cone 1204 is shown separately from the rest of the valve cone depicted in FIGS. 25A to 25C. Referring to FIG. 27A, the material of mesh cone 1204 may first be provided as a circular layer 1220 with a center cut out 1222 and a slit 1224 extending from the cut out 1222 to the periphery of the circle 1226. The slit 1224 provides a free edge so that the circular layer 1220 may subsequently be rolled to form mesh cone 1204. The cone shape of the mesh cone 1204 may be held by stitching, heat sealing, gluing, etc., the mesh material. The height (H) of the mesh cone 1204 may be between about 1.0 cm to about 2.0 cm, including all values and sub-ranges therein. For example, the height of the mesh cone may be about 1.0 cm, about 1.1 cm, about 1.2 cm, about 1.3 cm, about 1.4 cm, about 1.5 cm, about 1.6 cm, about 1.7 cm, about 1.8 cm, about 1.9 cm, or about 2.0 cm.

Figure 28A:
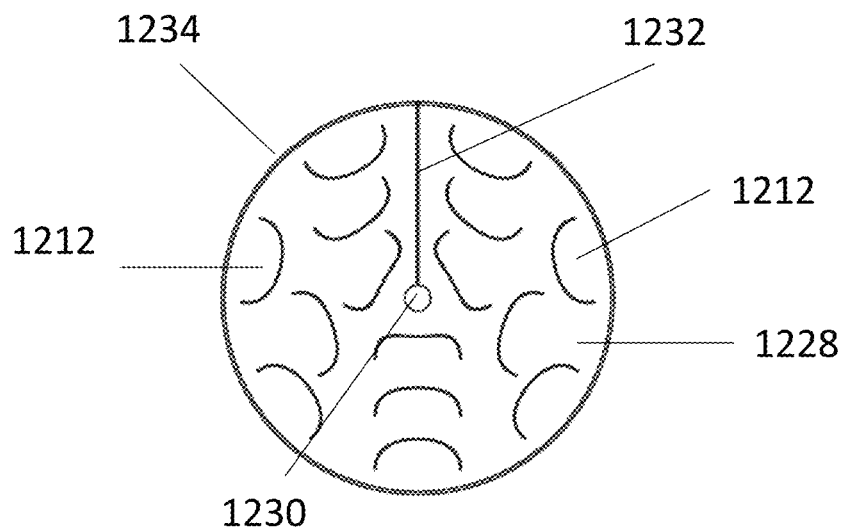
FIGS. 28A-28C depict the flow control cone of FIGS. 25A to 25C.
Figure 28B:
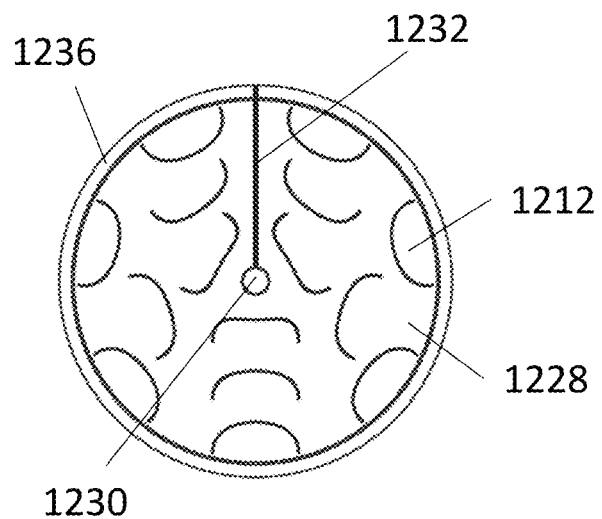
Figure 28C:
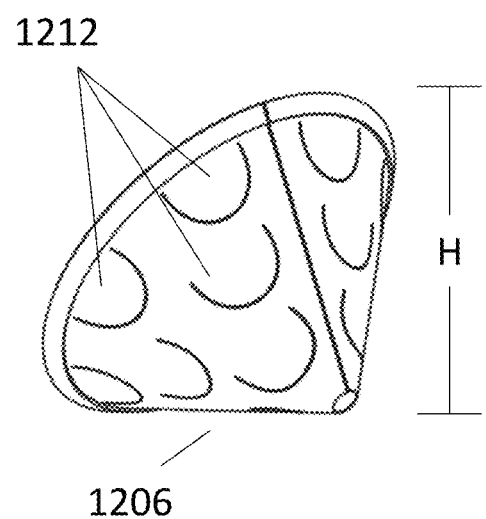

FIGS. 28A to 28C depict the flow control cone 1206 separately from the rest of the valve cone depicted in FIGS. 25A to 25C. Referring to FIG. 28A, the material of flow control cone 1206 may first be provided as a circular layer 1228 with a center cut out 1230 and a slit 1232 extending from the cut out 1230 to the periphery of the circle 1234. The slit 1232 provides a free edge so that the circular layer 1228 may later be rolled to form flow control cone 1206. Next, the flaps 1212 may be formed by laser cutting or stamping the flap shapes into the circular layer 1228. The flaps 1212 are shown as arc shaped in the figures, but may have any suitable size and shape, as previously stated. Referring to FIG. 28B, a rim 1236 may be created at the periphery of the circular layer 1228 by rolling the edge of the layer upon itself to create thickness at the periphery 1234, and then stitching, heat sealing, gluing, etc., the rolled edge to maintain the thickness in that area. After the rim 1236 is formed, the free edge of the slit 1232 is rolled to shape the circular layer 1228 into flow control cone 1206. The rim 1236 may help create a seal between the flow control cone 1206 and the interior surface of the housing during the pump stroke. The cone shape flow control cone 1206 may be held by stitching, heat sealing, gluing, etc., the mesh material. The height (H) of the flow control cone 1204 may be between about 1.0 cm to about 2.0 cm, including all values and sub-ranges therein. For example, the height of the flow control cone may be about 1.0 cm, about 1.1 cm, about 1.2 cm, about 1.3 cm, about 1.4 cm, about 1.5 cm, about 1.6 cm, about 1.7 cm, about 1.8 cm, about 1.9 cm, or about 2.0 cm.

In some variations, the pump may include an expandable housing comprising a plurality of openings or perforations in a body thereof, as previously mentioned. The openings may be through-wall openings in the body (e.g., through both the scaffold and layer), such that blood from the chamber of the body of the expandable housing may flow directly from within the chamber to outside of the chamber, without passing back through the inlet or through the outlet. When openings are included, a skirt may be coupled to or extend from an external surface of the expandable housing in a manner that surrounds, overlies or otherwise covers the plurality of openings to direct the blood flowing through the openings. For example, the skirt may be configured to generate retrograde blood flow directed toward the patient's heart during the pump stroke of a pumping cycle. The retrograde blood flow may help provide adequate perfusion of arteries branching from the aortic arch, for example, the carotid arteries and subclavian arteries.

Figure 19:
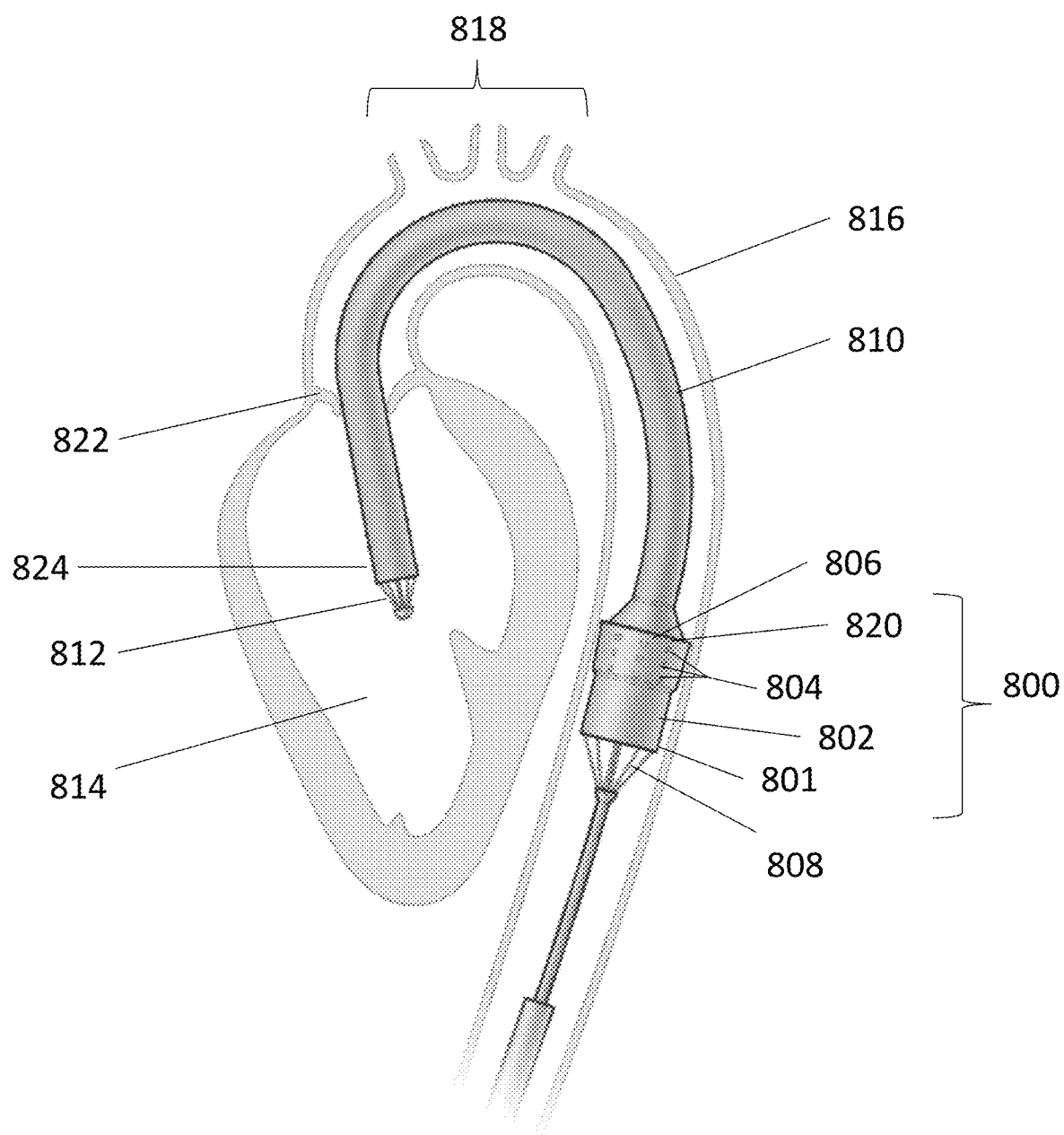
FIG. 19 depicts an exemplary pump comprising a housing that includes a plurality of openings and a skirt coupled to the housing.

Turning to FIG. 19, pump 800 may include an expandable housing 802 including a plurality of openings 804 and a cylindrical skirt 806 coupled to expandable housing 802 in a manner that spaces it therefrom. The skirt 806 may be coupled to and circumferentially (or partially circumferentially) surround an external surface of the housing 802, and may overlie at least a portion of the plurality of openings 804. The skirt 806 may be comprise a first diameter at its proximal end and a second larger diameter at its distal end, such that skirt 806 may be coupled to housing 802 at its proximal end, but then may be flared or spaced apart from the plurality of openings 804 formed in housing 802 to allow the retrograde flow of blood therethrough. Skirt 806 and expandable housing 802 may be integrally formed as a single piece, or they may be separate components coupled to one another by friction fit, an adhesive, welding, soldering, and/or the like. At the proximal end 801 of the expandable housing 802, an outlet 808 may be provided for anterograde blood flow to the body. A cannula 810 may be coupled to expandable housing 802 and may extend from the distal end of the housing 820 through the aorta 816 and aortic valve 822 into the left ventricle 814. At the distal end 824 of cannula 810, an inlet 812 for blood entry from the left ventricle 814 may be provided. The cannula may have varying lengths. Varying lengths may be used to accommodate such factors as different patient anatomy, patient size or age, desired location of pump placement, and/or point of access to the circulatory system. Although any suitable length may be utilized, the cannula may have a short, medium, or long length, as previously described. In FIG. 19, cannula 810 has a medium length, which ranges from about 25 cm to about 30 cm.

Figure 20:
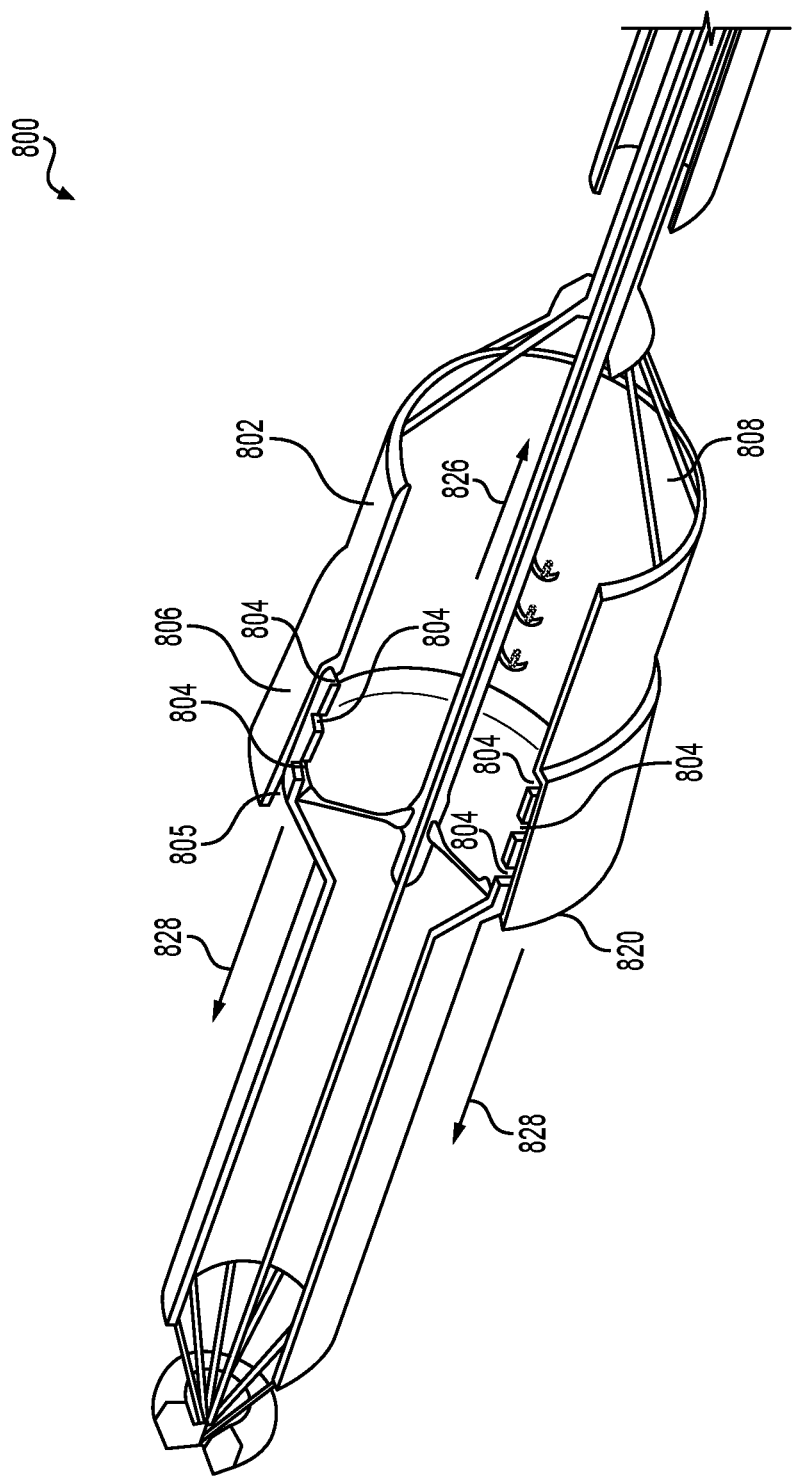
FIG. 20 depicts an enlarged view of the housing of FIG. 19 with a cut out to show how the skirt and plurality of openings work with the flexible diaphragm to generate retrograde blood flow.

Referring to FIG. 20, an enlarged view of pump 800 of FIG. 19 is shown. A cut out is provided in the expandable housing 802 to further show the structure and configuration of skirt 806 in relation to the plurality of openings 804. In FIG. 20, housing 802 includes a plurality of openings 804 at its distal end 820. Skirt 806 is concentrically disposed about the expandable housing 802 and overlies the plurality of openings 804. Additionally, skirt 806 is configured such that a space 805 is provided between the plurality of openings 804 and the skirt 806. In use, as flexible diaphragm 803 is moved toward outlet 808, blood within expandable housing 802 is pushed in the direction of arrow 826 through outlet 808 of expandable housing 802 and toward the feet of the patient. During movement of the flexible diaphragm 803, a first portion of blood is pushed through the plurality of openings 804 as the flexible diaphragm passes by them. The first portion of blood is pushed into space 805 and then directed by skirt 806 back toward the heart in the direction of arrows 828. As the flexible diaphragm 803 continues to move toward outlet 808, the portion of blood (second portion) remaining in the expandable housing 802 is pushed through outlet 808 toward the feet and to the rest of the body. The combination of the number of openings and the diameter of each opening may provide an amount of open surface area on the expandable housing for retrograde blood flow. Additionally, the skirt may be configured to adjust the amount of open surface area for retrograde flow by adjusting the number of patent (open) and closed openings. In general, a larger amount of open surface area may provide more retrograde blood flow toward the head of the patient, and a smaller amount of open surface area may provide a greater amount of anterograde blood flow to the body.

Figure 24A:
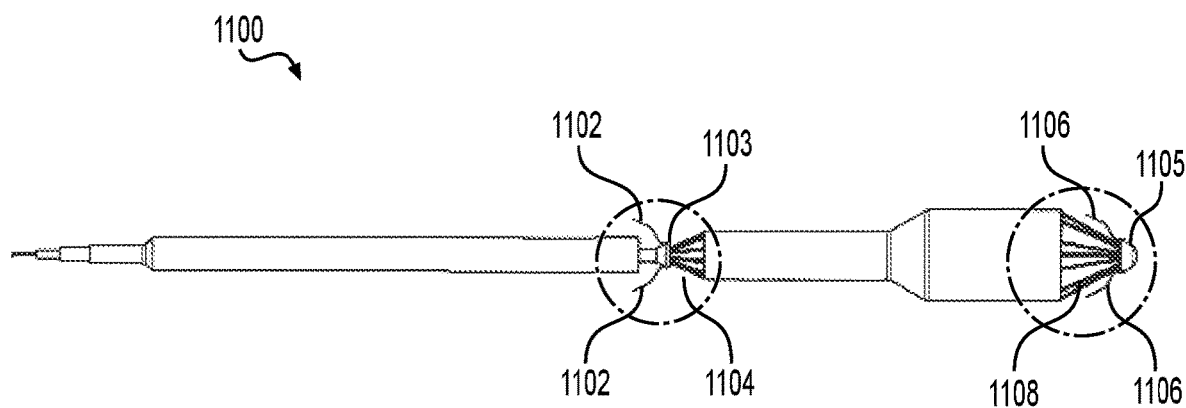
FIGS. 24A-24C depict exemplary locations for pressure sensor attachment to the pump.
Figure 24B:
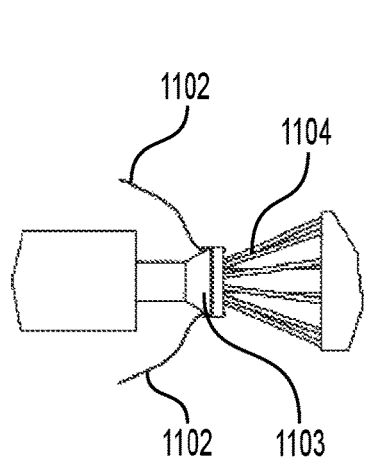
Figure 24C:
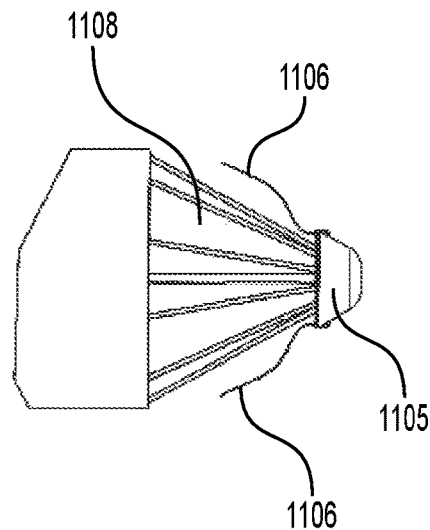

The pumps described herein may be driven by an external linear motor drive and linear motor controller situated at the end of a catheter external to the patient. The linear motor drive may be operatively coupled to the pump by a flexible cable or other flexible actuator running through the catheter. For example, as shown in FIG. 22A, pump 900 may be coupled to a linear motor drive 902 and linear motor controller 904 via catheter 906. Linear motor drive 902 and liner motor controller 904 may be situated outside the patient, within console 908. Catheter 906 may be coupled to the expandable housing 910 of pump 900, as shown in the close-up view in FIG. 22B. Here expandable housing 910 includes a plurality of openings 914 and a skirt 912 concentrically disposed about the openings 914. A cannula 916 may extend from the expandable housing 910 such that a distal end 918 of the cannula 916 may be positioned in the left ventricle 920. As shown in the close-up view in FIG. 22C, an inlet 922 may be provided at the distal end 918 of cannula 916. Inlet 922 may pull blood from the left ventricle 920 and into expandable housing 910 for pumping systemically. The linear motor controller 904 may further be configured to control pump 900. In some variations, linear motor controller 904 may be configured to control pump 900 via sensor feedback, such as, for example, pressure sensor feedback. For example, as described above, one or more pressure sensors (not shown) may be mounted in or on inlet 922 of cannula 916, and one or more pressure sensors may be mounted in or on outlet 924 of expandable housing 910. In some variations, two pressure sensors may be mounted in or on the inlet 922 and/or outlet 924 for redundancy. For example, referring to FIG. 24A, pump 1100 may include two pressure sensors 1102 on the distal end of an inner sheath 1103 at the pump outlet 1104, and another two pressure sensors 1106 may be disposed on a nose cap 1105 at the pump inlet 1108. FIGS. 24B and 24C show enlarged views of the pressure transducers at the pump outlet 1104 and pump inlet 1108. The controller 904 may be configured to have predetermined high and low blood pressure set points. When measurements from the pressure transducers indicate that blood pressure has dropped below the low set point, the controller 904 may increase the speed of the linear reciprocation, and/or when measurements from the pressure transducers indicate that blood pressure has increased above the high set point, the controller 904 may decrease the speed of the linear reciprocation to thereby reduce flow and return blood pressure back within a target range.

Turning to FIGS. 23A-23C, in some variations, a pump may be disposed external to the body, for example, within a console at the patient's bedside. A coaxial catheter may be coupled to the pump at one end and inserted into the patient at the other end so that blood flows between the patient and the external pump. The coaxial catheter may include an inflow lumen and an outflow lumen. Similar to that described for FIG. 22A, an external pump may be driven by a linear motor drive and linear motor controller situated at the end of the coaxial catheter external to the patient. The linear motor drive may be operatively coupled to the pump by any suitable connector or fitting, e.g., a quick connect coupler. For example, as shown in FIG. 23A, external pump 1000 may be coupled to a coaxial catheter 1006 via inlet and outlet tubes 1016. Pump 1000 may also be coupled to a linear motor drive 1002 and linear motor controller 1004 within console 1008. Console 1008 may also comprise a power supply 1010, a battery 1012, and/or a user interface 1014. The coaxial catheter may include an inflow lumen 1018 and an outflow lumen 1020, as shown in the close-up view provided in FIG. 23B. The distal end of coaxial catheter 1006 is illustrated in the close-up view provided in FIG. 23C, where blood is shown being pulled from the left ventricle 1024 into inflow lumen 1018 at a pump intake end, and pushed out of outflow lumen 1020 at a pump exhaust end right above the aortic valve 1022. The linear motor controller 1004 may further be configured to control the pump 1000 via pressure transducer feedback, as described in more detail herein. For example, one or more pressure transducers (not shown) may be mounted in or on inflow lumen 1018, and another pressure transducer mounted in or on outflow lumen 1020. In some variations, two pressure transducers may be mounted in or on the inflow and outflow lumens for redundancy.

Methods

Methods for pumping blood using a linear reciprocating pump are also described herein. Utilizing a linear pump, as opposed to a rotary pump, may help avoid the shear forces that cause red blood cell damage, and may pump blood in a pulsatile fashion, mimicking the natural pumping cycle of the heart. In order for the pump to generate sufficient blood pressure to move blood peripherally, a linearly reciprocating member may be configured such that a seal is created between it and the pump housing during a pump stroke of the pumping cycle. The pumps may be placed in various parts of the circulatory system of a patient, such as the left ventricle, the right ventricle, and the aorta. However, in some instances it may be useful to have the pump lie external to the patient. The linear reciprocating pumps may be placed to assist with heart failure due to, e.g., myocardial infarction, hypertension, trauma, and cardiac anomalies.

As a first step, the methods may include accessing the circulatory system of a patient. Access may generally be accomplished using the Seldinger technique whereby a guidewire is placed within a desired artery or vein and the pump advanced over the guidewire to a target location. Arterial access may be obtained, e.g., from the femoral artery or the carotid artery. Arterial access may be useful when the target location for the pump is the left ventricle or aorta. Venous access may be obtained, e.g., from the femoral vein or internal jugular vein. Venous access may be useful when the target location for the pump is the right ventricle. The guidewire may be slidingly advanced through the lumen of a pump actuator such as a drive line, cable, or rod, which linearly reciprocates a valve member, for example, a valve cone or a flexible diaphragm, within the expandable housing of the pump.

The methods may also include advancing a pump to a target location within the circulatory system of a patient, where the pump includes an expandable housing comprising an outer surface, an interior surface, an expanded configuration, and a collapsed configuration. The pump may further include a valve member. In some variations, the valve member may be a valve cone including a flow control layer and a mesh layer coupled to an expandable frame. In other variations, the valve member may be a flexible diaphragm comprising a diaphragm body and a rim disposed within the expandable housing, where the flexible diaphragm has an extended configuration and a collapsed configuration. Once at the target location, the expandable housing may be expanded from the collapsed configuration to the expanded configuration, and the valve cone or the flexible diaphragm contained therein linearly reciprocated to generate a fill stroke and a pump stroke of a pumping cycle. When the pump further comprises a cannula, the cannula may be advanced through the aortic valve and into the left ventricle of the patient. Non-limiting examples of target locations for the expandable housing and flexible diaphragm include the aortic arch, the descending aorta, the thoracic aorta, and the abdominal aorta.

The expandable housing and the valve members (e.g., the valve cone and the flexible diaphragm) may be in their collapsed configurations within an outer sheath and inner sheath, respectively, during advancement within the vasculature. In some variations, once the expandable housing has been positioned at the target location, the outer sheath may be retracted to allow the housing to expand from the collapsed configuration to the expanded configuration. In other variations, the expandable housing may be advanced out of the housing, e.g., using a pusher, thereby allowing the housing to expand from the collapsed configuration to the expanded configuration. The inner sheath, which may be concentrically disposed about the valve cone or the flexible diaphragm, may then be retracted to allow the valve cone or the diaphragm to expand from the collapsed configuration to the expanded or extended configuration. When the pump comprises a support member such as an expandable frame, withdrawal of the inner sheath may also allow the frame to expand from the collapsed configuration to the expanded configuration. When the pump comprises a support member such as a tine support, withdrawal of the inner sheath may also allow the plurality of tines to expand from the compressed configuration to the expanded configuration.

The pump may be reciprocated within the expandable housing under the force of a reciprocating actuator (e.g., drive cable) to initiate a succession of fill strokes and pump strokes. In variations where the valve member is a flexible diaphragm, during each fill stroke of the pump, the flexible diaphragm may be collapsed, allowing blood to flow past the diaphragm (with or without supporting tines) to fill the expandable housing. During each pump stroke of the pump, the flexible diaphragm may return to its extended configuration, forcing blood out from the expandable housing. In variations where the valve member is a valve cone including a flow control layer and a mesh layer, during each fill stroke of the pump, the flaps in the flow control layer open and the openings in the mesh allow blood to flow through the valve cone to fill the expandable housing. During each pump stroke of the pump, the flaps return to their closed configuration and are supported by the mesh layer to remain closed against the pressure of the blood as the blood is forced out of the expandable housing. The reciprocating motion of the drive cable and pulsatile pump may be controlled by a programmable linear motor controller to provide the desired blood flow and pressure characteristics. In some variations, the linear motor controller may be configured to control the pump via sensor (e.g., pressure transducer) feedback as described in more detail herein.

During the pump stroke, contact between the rim of the valve cone or flexible diaphragm and the inner surface of the expandable housing may be maintained such that a seal is created to prevent blood flow between the rim and interior surface. Additionally, during the pump stroke, blood may be pulled into the expandable housing. Depending on the variation of pump used, blood may be pulled into the expandable housing from the left ventricle or the aorta. The pump stroke may generally push blood out of the expandable housing into a portion of the aorta, for example, the ascending aorta or the descending aorta. When the expandable housing and flexible diaphragm are situated outside the patient, blood may be pushed through the coaxial catheter coupled thereto to the ascending aorta, right above the aortic valve. During the pumping cycle, the valve cone or the flexible diaphragm may be collapsed to the collapsed configuration during the fill stroke and expanded to the expanded or extended configuration during the pump stroke.

The pump may be advanced and positioned in various parts of the circulatory system of the patient. In one variation, the pump may be advanced until the expandable housing and pulsatile portion of the pump (e.g., the flexible diaphragm with or without tines) is located within the left ventricle and a cannula extending from the proximal end of the expandable housing extends through the aortic valve. In this variation, blood may flow through a proximal inlet of the expandable housing to fill the expandable housing during the fill stroke (rearward movement of the flexible diaphragm toward the feet). Blood then exits a distal outlet of the expandable housing to provide blood to the body during the pump stroke (forward movement of the flexible diaphragm toward the head).

Figure 2:
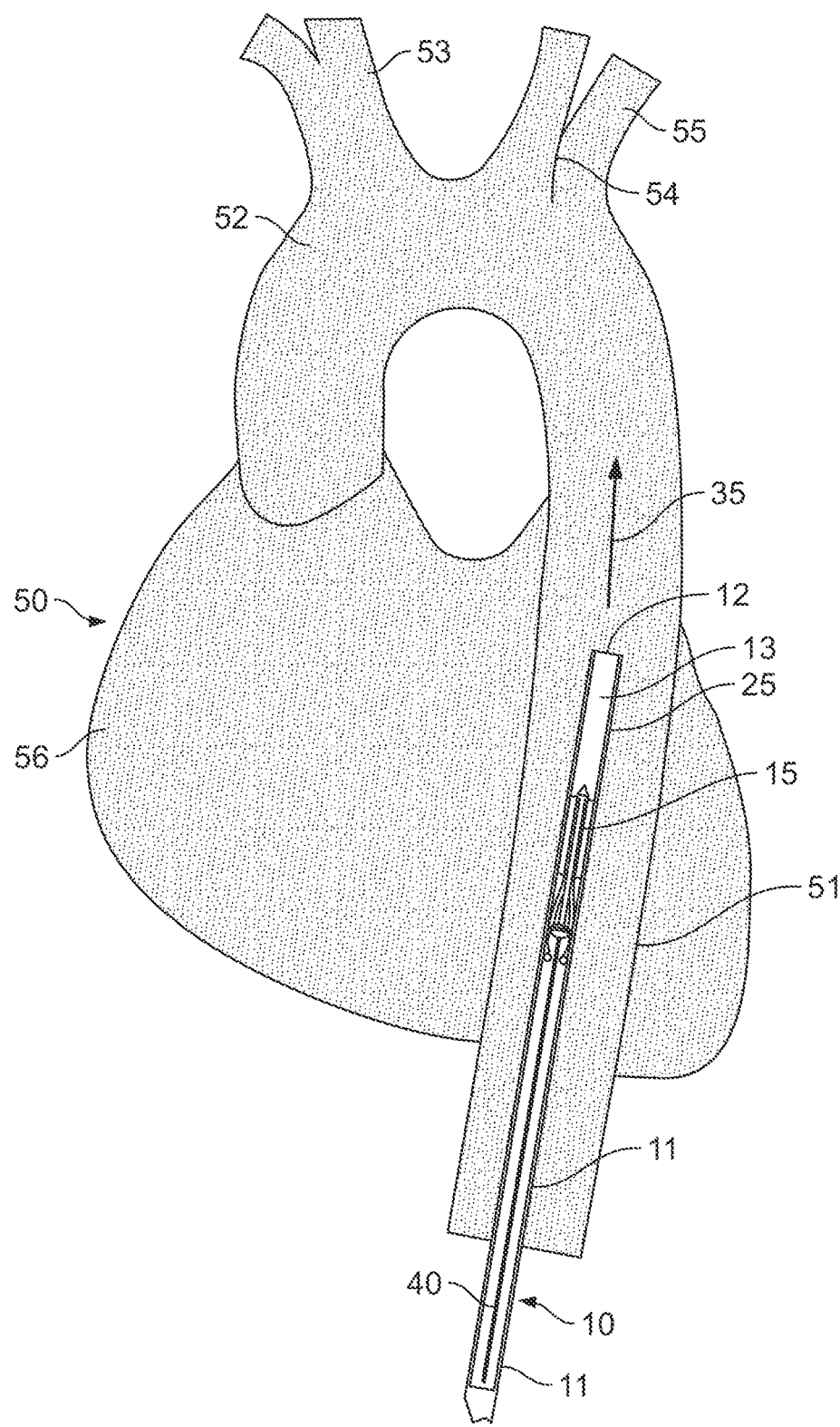
FIG. 2 depicts the pump of FIG. 1 being advanced within the aorta to a left ventricle of the heart.

For example, as illustrated in FIG. 2, a pump 10 may be advanced in its collapsed configuration within a patient's aorta to the left ventricle. Heart 50 includes a left ventricle 56, which fluidly communicates with an ascending aorta 52 and a descending aorta 51. Ascending aorta 52 further supports a plurality of arteries such as arteries 53 (brachiocephalic artery), 54 (left common carotid artery), and 55 (left subclavian artery). In FIG. 2, pump 10 is advanced to the left ventricle through the descending aorta 51 in the direction of arrow 35. As described above, pump 10 may include an outer sheath 11 through which a drive cable 40 may pass. As also described above, pump 10 may define an end 12 within which a bearing 13 may be supported. An expandable housing 25 (better seen in FIG. 3) may be deployed from the outer sheath 11 and may also fixedly support bearing 13. Tine support 15 including a plurality of tines 20 may be coupled to the end of drive cable 40 and may be captivated within an outer sheath 11 in the manner set forth above in FIG. 1.

Figure 3:
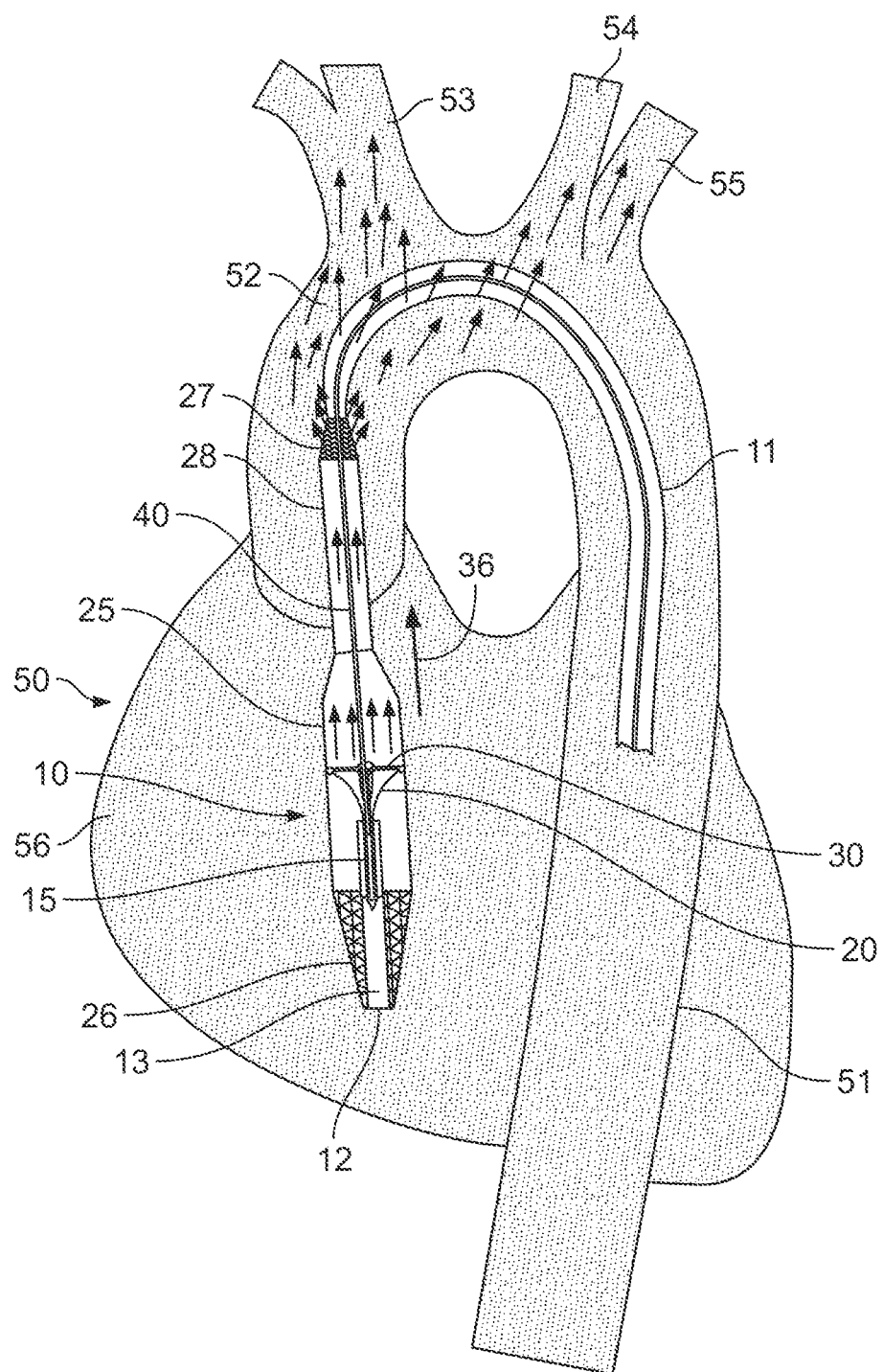
FIG. 3 illustrates the movement of blood resulting from a pumping stroke of the pump of FIG. 2.

Once pump 10 is positioned within the left ventricle 56, it assumes the operational position shown in FIG. 3. Here expandable housing 25 has been expanded to its expanded configuration and thus is shown to include a distal inlet (mesh portion) 26 and a proximal outlet (mesh portion) 27. Proximal outlet 27 is provided at the end of the cannula (housing extension) 28 extending from the expandable housing 25 and through the aortic valve into the ascending aorta 52. With this configuration, blood is pulled into the expandable housing 25 from the left ventricle 56 during the fill stroke, and moved out of the expandable housing 25 in the direction of the arrows to the ascending aorta 52 and arteries 53, 54, and 55 during the pump stroke.

The pumping action of pump 10 may be undertaken by activating the linear motor 19 (seen in FIG. 1) to initiate a reciprocating action of tine support 15 (and the plurality of tines 20) by successive forces pushing and pulling on flexible cable 40. The pumping action of pump 10 is set forth below in FIGS. 8 and 9 in greater detail. However, suffice it to note here that FIG. 3 generally illustrates the operation of pump 10 during a pump stroke, which is characterized by a pulling force upon drive cable 40 and movement of the tine support 15 in the direction indicated by arrow 36. During this pump stroke, it will be noted that diaphragm 30 has extended to its fully open configuration and thus exerts a driving force against blood within expandable housing 25, forcing blood upwardly through cannula (housing extension) 28 and outwardly through proximal outlet (mesh portion) 27, and creating blood flow through ascending aorta 52 and outwardly to the patient's body through arteries such as arteries 53, 54 and 55. Referring to FIG. 4, it will be noted that a push force against drive cable 40 in the direction indicated by arrow 37 therein produces a fill stroke during which diaphragm 30 is collapsed and blood flows into expandable housing 25 through distal inlet 26.

With cardiac assist pulsatile pump 10 remaining positioned within the left ventricle and aorta and expandable housing 25 remaining configured for operation, the pumping action of pump 10 continues as linear motor 19 (seen in FIG. 1) continues the reciprocating action of tine support 15 (and the plurality of tines 20) by successive forces pushing and pulling on flexible cable 40. Once again it will be understood that the pumping action of pump 10 is set forth below in FIGS. 8 and 9 in greater detail. However, suffice it to note here that FIG. 4 illustrates the operation of pump 10 during a fill stroke characterized by a pushing force upon drive cable 40 moving tine support 15 in the direction indicated by arrow 37. During this fill stroke, it will be noted that diaphragm 30 has partially collapsed and thus exerts a reduced force against blood within expandable housing 25. As a result, blood is able to flow inwardly through distal inlet (mesh portion) 26 filling the interior of expandable housing 25. For purposes of illustration, and with temporary return to FIG. 3, it will be recalled that a pull force against drive cable 40 in the direction indicated by arrow 36 therein produces a pump stroke during which diaphragm 30 is expanded and blood flows outwardly from expandable housing 25. Accordingly, with simultaneous reference to FIGS. 3 and 4, the pumping action of pump 10 may be illustrated by alternating the pump stroke shown in FIG. 3 and the fill stroke shown in FIG. 4.

Figure 18A:
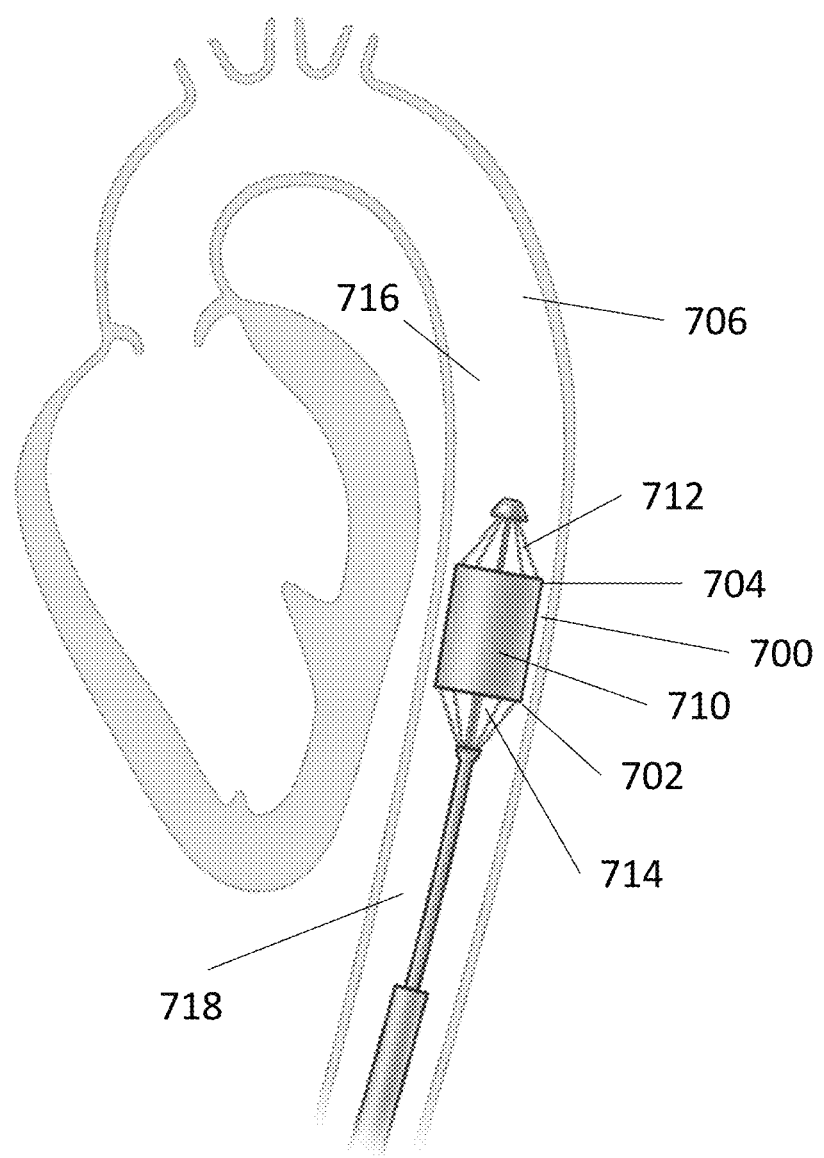
FIGS. 18A and 18B depict a pump according to another variation, where the housing lacks a cannula extending therefrom.
Figure 18B:
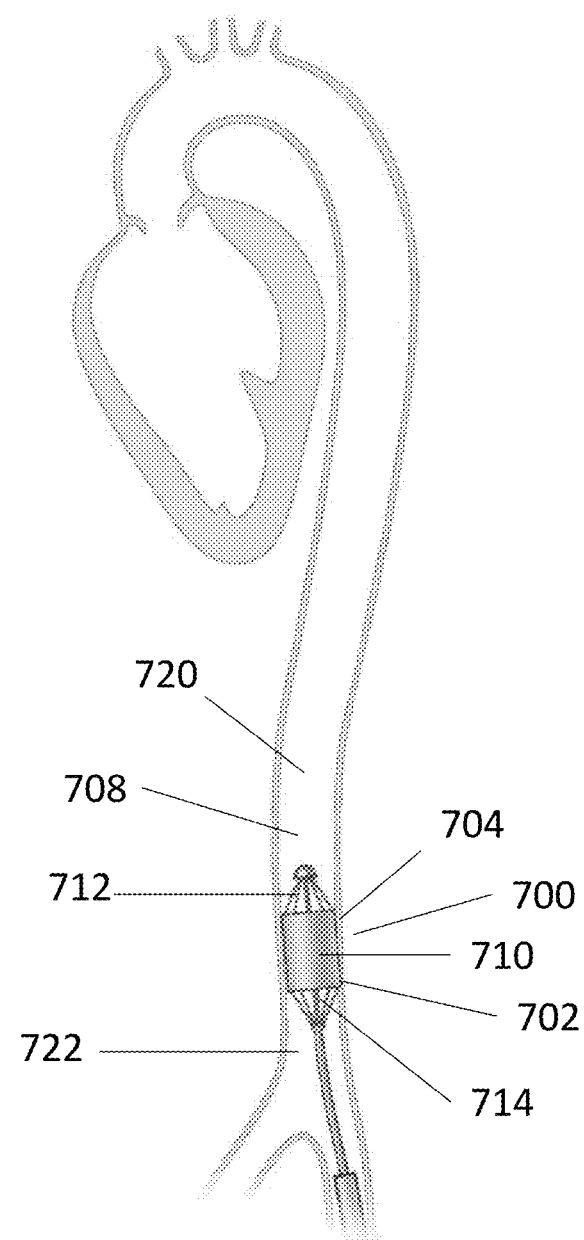

Some pump variations do not include a cannula extending from the expandable housing. For example, pump 100 in FIGS. 5, 6 and 7, is substantially identical to pump 10 in FIGS. 3 and 4 both in structure and function, except for the lack of cannula (extended portion) 28. In addition, as shown in FIGS. 18A and 18B, pump 700 does not include a cannula extending from either the proximal end 702 or distal end 704 of the expandable housing 710, but is otherwise substantially identical to pump 100. Exemplary target locations for pumps 100 and 700 may be the thoracic aorta 706 (FIG. 18A) or the abdominal aorta 708 (FIG. 18B). In FIG. 5, blood from one portion of the aorta enters the expandable housing 60 via inlet 63 and is pumped to a second portion of the aorta upon exiting outlet 64 of the expandable housing 60. Referring to FIG. 18A, blood from one portion 716 of the thoracic aorta 706 enters the expandable housing 710 via inlet 712 and is pumped to a second portion 718 of the thoracic aorta 706 upon exiting outlet 714 of the expandable housing 710. In FIG. 18B, blood from one portion 720 of the abdominal aorta 708 enters the expandable housing 710 via inlet 712 and is pumped to a second portion 722 of the abdominal aorta 708 upon exiting outlet 714 of the expandable housing 710.

By way of overview, FIGS. 5, 6 and 7 set forth sequential section views of the pulsatile pump 100 illustrating the transition of the pulsatile pump portion between its compacted configuration utilized during catheter insertion and its expanded operational configuration utilized during pumping action. Thus, FIG. 5 shows a section view of linear cardiac assist tile pump 100 in its collapsed configuration while FIG. 7 shows a section view of pump 100 in its expanded operational configuration. FIG. 6 sets forth a section view of pump 100 at a point intermediate between the configurations shown in FIGS. 5 and 7.

Figure 8:
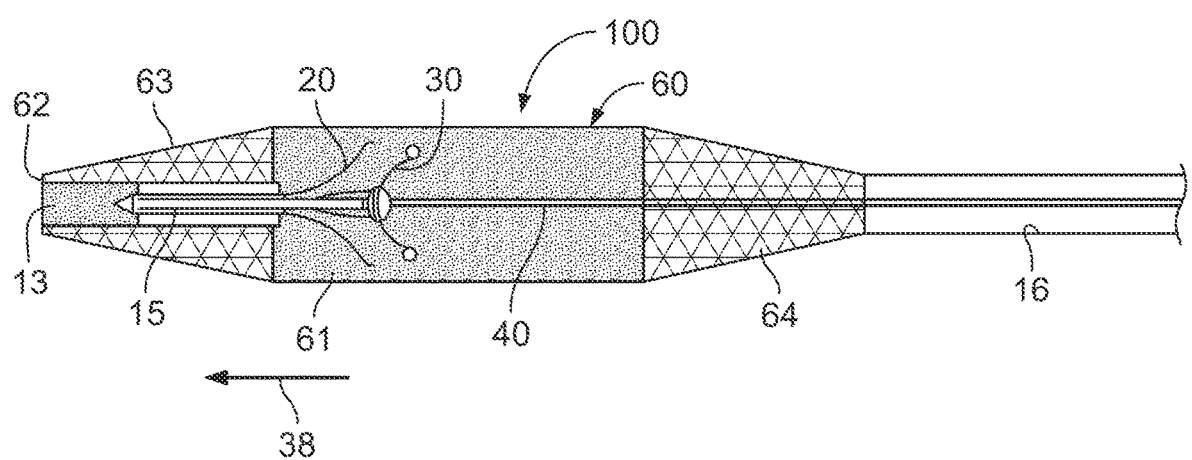
FIG. 8 depicts an enlarged cross-sectional view of the pump of FIG. 1 during a filling stroke portion of its pumping operation.
Figure 9:
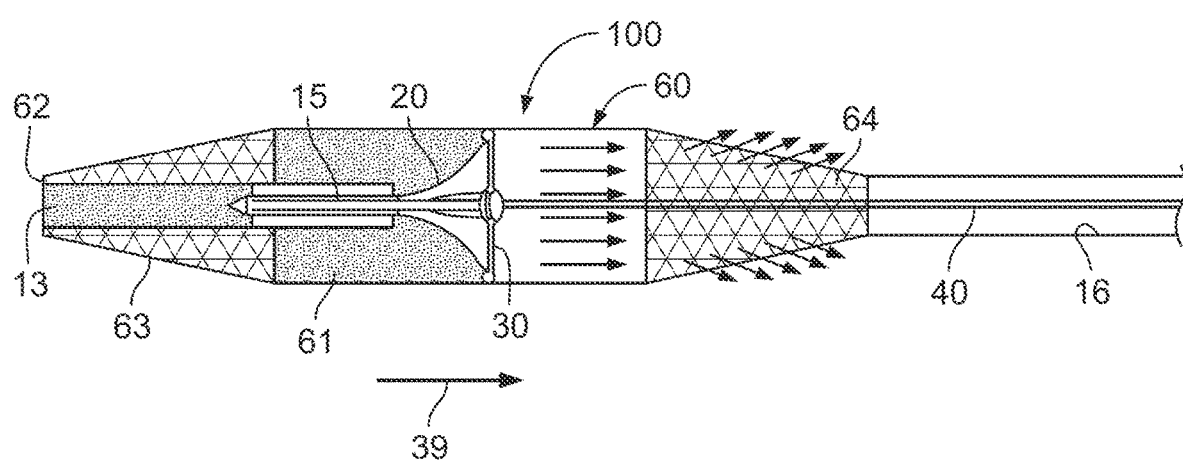
FIG. 9 depicts an enlarged cross-sectional view of the pump of FIG. 1 during a pumping stroke portion of its pumping operation.

FIGS. 8 and 9 set forth section views of pump 100 in operation. FIG. 8 sets forth a section view of pump 100 during a fill stroke while FIG. 9 sets forth a section view of pump 100 during a pump stroke. The succession of fill and pump strokes are carried forward on a repeated basis to produce pulsatile pumping action as the linear motor (linear motor 19 seen in FIG. 1) reciprocates drive cable 40 and thereby reciprocates the pumping mechanism within pump 100.

With specific reference to FIG. 8 pump 100 includes an expandable housing 60 having an end 62 supporting a bearing 13 and inlet (scaffold portion) 63. Expandable housing 60 further includes a chamber 61 and an outlet (scaffold portion) 64. The chamber may be formed by embedding a portion of the scaffold of expandable housing 60 within a polymer layer (e.g., overmolding) or coupling a fabric layer to the scaffold, as previously described. Tine support 15 may be slidably received within bearing 13 and joined to the interior end of a drive cable 40. Tine support 15 supports a plurality of tines 20 and a flexible diaphragm 30. Tine support 15 may define a plurality of outwardly extending spline ribs between which spline grooves are formed. The spline grooves provide blood flow paths by which blood is able to flow past tine support 15.

As mentioned, FIG. 8 shows a fill stroke in the operation of pump 100. Accordingly, the reciprocating force applied to drive cable 40 moves tine support 15 in the direction indicated by arrow 38. Because blood is present within chamber 61, the movement of tine support 15 in the direction indicated by arrow 38 causes a force against the back side of diaphragm 30 which in turn flexes it in the manner shown. The flexing of diaphragm 30 away from its outwardly extended position (seen in FIG. 9) allows blood flow around tines 20 and diaphragm 30 within chamber 61. This provides a filling of chamber 61 with blood drawn through inlet portion 63 and bearing 13. Once tine support 15 reaches the end of its filling stroke, the drive apparatus described above applies a pulling force to drive cable 40 initiating a pump stroke shown in FIG. 9.

With specific reference to FIG. 9 pump 100 includes an expandable housing 60 having an end 62 supporting a bearing 13 and an inlet (scaffold portion) 63. Expandable housing 60 further includes a chamber 61 and an outlet (scaffold portion) 64. Tine support 15 is slidably received within bearing 13 and is joined to the interior end of a drive cable 40. Tine support 15 includes a plurality of tines 20 and a flexible diaphragm 30. Tine support 15 defines a plurality of outwardly extending spline ribs between which spline grooves are formed. The spline grooves provide blood flow paths by which blood is able to flow past tine support 15.

As mentioned, FIG. 9 shows a pump stroke in the operation of pump 100. Accordingly, the reciprocating force applied to drive cable 40 moves tine support 15 in the direction indicated by arrow 39. Because blood is present within chamber 61, the movement of tine support 15 in the direction indicated by arrow 39 causes a force against the front side of diaphragm 30 which in turn forces diaphragm 30 against tines 20 the extended position shown. The extension of diaphragm 30 to its outwardly extended position forces blood from chamber 61 ahead of diaphragm 30 as diaphragm 30 moves in the direction indicated by arrow 39. This in turn creates a blood flow outwardly from chamber 61 through outlet 64. Once the tine support 15 reaches the end of its pump stroke, the drive apparatus described above applies a pushing force to drive cable 40 initiating the next fill stroke shown in FIG. 8. As the drive apparatus described above reciprocates, alternate push and pull forces against cable 40 are generated that correspond to successive fill and pump strokes of pump 100, which produce a pulsatile blood flow.

Figure 21:
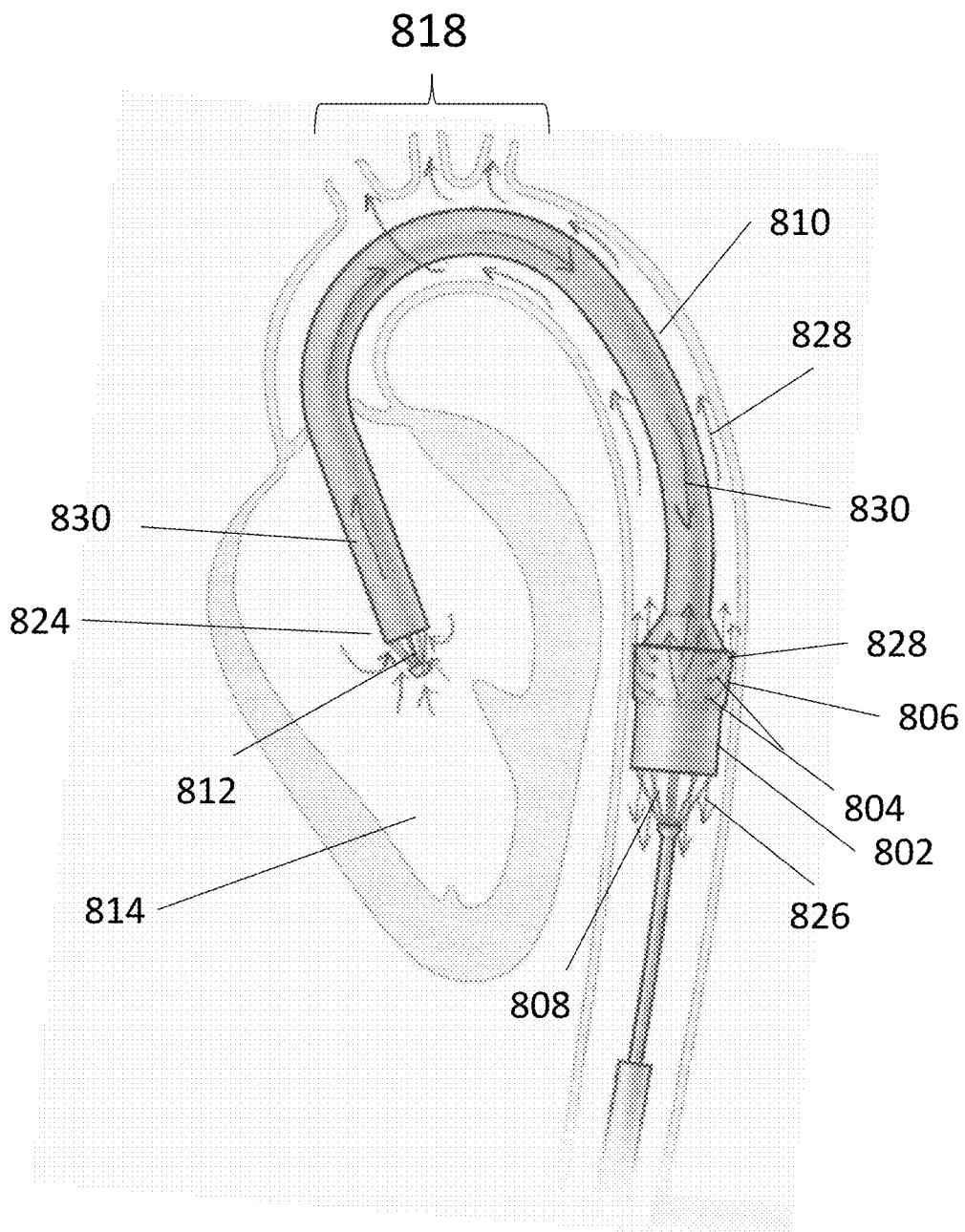
FIG. 21 illustrates how blood flows during a pumping cycle including retrograde and anterograde flow.

As previously described, the expandable housing in some variations may comprise a plurality of openings and a skirt coupled to the expandable housing. In this instance, blood exiting the openings may be directed in a retrograde direction toward the heart of the patient during the pump stroke by the skirt. The retrograde blood flow may help provide adequate perfusion of arteries branching from the aortic arch, for example, the carotid arteries and subclavian arteries. The ability to maintain adequate perfusion of the subclavian artery may prevent flow reversal from the vertebrobasilar artery to the subclavian artery, a phenomenon known as "subclavian steal." For example, referring to FIG. 21, pump 800 may pull blood from the left ventricle 814 through inlet 812 provided at the distal end 824 of cannula 810, which may extend from expandable housing 802. From the inlet 812, blood may flow in the direction of arrows 830 to fill expandable housing 802. During a pump stroke, blood from the expandable housing 802 may generally be moved toward outlet 808 in the direction of arrows 826. However, as blood is moved past the plurality of openings 804, a first portion of blood may be pushed through openings 804 and then directed by skirt 806 back toward the heart in the direction of arrows 828 to perfuse vessels 818 branching from the aortic arch. The portion of blood (second portion) not pushed out of the expandable housing through the plurality of openings 804, and remaining in the expandable housing 802 is pushed through outlet 808 toward the feet and to the rest of the body.

The length of the skirt may be adjusted to achieve a predetermined amount of retrograde blood flow toward the heart of the patient. Alternatively, the number of openings may be adjusted to achieve a predetermined amount of retrograde blood flow toward the head of the patient. The diameter of the openings may also be adjusted to achieve a predetermined amount of retrograde blood flow toward the head of the patient. The combination of the number of openings and opening diameter may provide an amount of open surface area on the expandable housing for retrograde blood flow. Accordingly, adjustment of any one or combination of the foregoing features may be utilized so that about 60% of the blood from the pump stroke flows in a retrograde direction toward the heart of the patient about 50% of the blood from the pump stroke flows in a retrograde direction toward the heart of the patient, or about 40% of the blood from the pump stroke flows in a retrograde direction toward the head of the patient.

In some variations, the skirt may be configured to adjust the amount of open surface area for retrograde flow by adjusting the number of patent (open) and closed openings. For example, a tether may be coupled to the skirt and configured to open and close the skirt against the expandable housing similar to how a noose can be tightened and loosened. The amount of opening or closing may be adjusted using a rotatable dial disposed, e.g., on a console external to the patient. In general, a larger amount of open surface area may provide more retrograde blood flow toward the head and heart of the patient, and a smaller amount of open surface area may provide a greater amount of anterograde blood flow to the body.

Other methods for pumping blood may include advancing a pump to a target location within the aorta of a patient, such as the thoracic aorta or the abdominal aorta, where the pump has a fill stroke and a pump stroke; pulling a fill volume of blood into the pump during the pump stroke; and pushing an exit volume of blood out of the pump during the pump stroke, where the exit volume comprises a first portion of blood and a second portion of blood. The fill stroke may pull blood from the left ventricle of the patient. Additionally, the first portion of blood may be pumped in a retrograde direction toward the head of the patient, and the second portion of blood may be pumped in an anterograde direction. The second portion of blood may be about 60% of the exit volume, about 50% of the exit volume, or about 40% of the exit volume.

When the pump is disposed external to the patient, the method for pumping blood may include accessing the circulatory system of a patient with a coaxial catheter. The external pump may include the same valve member, e.g., a valve cone or a flexible diaphragm, as the internal pumps placed within the vasculature or a heart chamber, but the housing may not be expandable. The valve cone or flexible diaphragm contained within the expandable housing may comprise a body and a rim. The flexible diaphragm may have an extended configuration and a collapsed configuration, and the valve cone may have an expanded configuration and a collapsed configuration. The external pump may be disposed within a console comprising a user interface. The coaxial catheter may comprise an inflow lumen and an outflow lumen. The coaxial catheter may be coupled to the external pump at one end, and the other end inserted and advanced within the patient.

Access to the circulatory system with a coaxial catheter may be obtained from any suitable artery or vein, for example, the femoral artery, the subclavian artery, the carotid artery, or the jugular vein. Once access is obtained, the coaxial catheter may be advanced to a target location in the circulatory system and the flexible diaphragm linearly reciprocated within the housing to generate a fill stroke and a pump stroke of a pumping cycle. During the pump stroke, contact between the rim of the valve cone or the flexible diaphragm and the interior surface of the housing may be maintained to create a seal therebetween and prevent blood from flowing around the valve cone or the flexible diaphragm. The seal may help generate and maintain the force of the pump stroke as well as minimize red blood cell damage that may occur with blood flowing between a space existing between the rim and the interior surface. The methods described herein may include advancing a coaxial catheter to various target locations in a patient. For example, the target location for the inflow lumen of the coaxial catheter may be a left ventricle of the patient, and the target location for the outflow lumen of the coaxial catheter may be above an aortic valve of the patient.

For example, as shown in FIG. 23A, external pump 1000 is coupled to a coaxial catheter 1006 by inlet and outlet tubes 1016. Coaxial catheter 1006 includes an inflow lumen 1018 and an outflow lumen 1020, as shown in the close-up view provided in FIG. 23B. Access to the circulatory system by coaxial catheter 1006 is via the femoral artery 1026. Once access is obtained, coaxial catheter 1006 is advanced to the left ventricle 1024. More specifically, and as shown in the close-up view of FIG. 23C, the distal end of coaxial catheter 1006 is advanced until the inflow lumen 1018 is within the left ventricle and the outflow lumen 1020 is situated above the aortic valve. In FIG. 23C, blood is shown as being pulled from the left ventricle 1024 into inflow lumen 1018 at a pump intake end, and pushed out of outflow lumen 1020 at a pump exhaust end right above the aortic valve 1022. Pump 1000 is also coupled to a linear motor drive 1002 and linear motor controller 1004 within console 1008. Console 1008 also includes a power supply 1010, a battery 1012, and a user interface 1014. The linear motor controller 1004 may be configured to control the speed of the pump 1000 via pressure transducer feedback. For example, a pressure transducer (not shown) may be mounted in or on inflow lumen 1018, and another pressure transducer mounted in or on outflow lumen 1020. In some variations, two pressure transducers may be mounted in or on the inflow and outflow lumens for redundancy in case one fails. The controller may be configured to have predetermined high and low blood pressure set points. When measurements from the pressure transducers indicate that blood pressure has dropped below the low set point, the controller 1004 would increase the speed of the linear reciprocation, and if too high (e.g., above the high set point), the controller 1004 would slow the speed of the linear reciprocation to thereby reduce flow and blood pressure back within a target range.

The foregoing description, for purposes of explanation, used specific nomenclature to provide a thorough understanding of the invention. However, it will be apparent to one skilled in the art that specific details are not required in order to practice the invention. Thus, the foregoing descriptions of specific embodiments of the invention are presented for purposes of illustration and description. They are not intended to be exhaustive or to limit the invention to the precise forms disclosed; obviously, many modifications and variations are possible in view of the above teachings. The embodiments were chosen and described in order to explain the principles of the invention and its practical applications, they thereby enable others skilled in the art to utilize the invention and various embodiments with various modifications as are suited to the particular use contemplated.

The invention claimed is:

1. A pump for assisting blood circulation comprising:
a housing comprising an interior surface and an expanded configuration;
a valve member comprising a rim disposed within the housing, wherein the valve member has an expanded or extended configuration, and a collapsed configuration; and
an actuator coupled to the valve member, wherein the actuator is configured to linearly reciprocate the valve member within the housing,
wherein the pump is configured for advancement within the circulatory system and has a fill stroke and a pump stroke, and wherein the rim of the valve member is configured to maintain contact with the interior surface of the housing during the pump stroke.

2. The pump of claim 1, wherein the valve member comprises a valve cone.

3. The pump of claim 2, wherein the valve cone comprises a plurality of material layers coupled to an expandable frame.

4. The pump of claim 3, wherein the plurality of material layers comprises a mesh layer.

5. The pump of claim 4, wherein the mesh layer comprises a woven fabric.

6. The pump of claim 4, wherein the mesh layer comprises an elastomeric polymer.

7. The pump of claim 6, wherein the elastomeric polymer comprises a silicone, a polyester, a polyurethane, or a combination thereof.

8. The pump of claim 3, wherein the plurality of material layers comprises a flow control layer, the flow control layer comprising a plurality of flaps having an open configuration and a closed configuration.

9. The pump of claim 8, wherein the flow control layer comprises 15 flaps.

10. The pump of claim 8, wherein the plurality of flaps have a semi-circular shape or an arc shape.

11. The pump of claim 8, wherein the plurality of flaps are in the open configuration during the fill stroke.

12. The pump of claim 8, wherein the plurality of flaps are in the closed configuration during the pump stroke.

13. The pump of claim 8, wherein the flow control layer comprises a body, and the rim is formed by rolling an edge of the body.

14. The pump of claim 13, wherein a thickness of the rim is greater than a thickness of the body.

15. The pump of claim 13, wherein the body has a thickness ranging from about 0.03 mm to about 0.05 mm.

16. The pump of claim 1, wherein the rim has a thickness ranging from about 0.20 mm to about 1.5 mm.

17. The pump of claim 3, wherein each of the layers of the plurality of material layers has a conical shape.

18. The pump of claim 3, wherein the expandable frame has a conical shape in its expanded configuration.

19. The pump of claim 3, wherein the expandable frame comprises stainless steel, nickel, titanium, or an alloy thereof.

20. The pump of claim 13, wherein the body of the flow control layer and the rim comprise the same material.

21. The pump of claim 1, wherein the housing is expandable and comprises a scaffold, the scaffold comprising a proximal end and a distal end.

22. The pump of claim 21, wherein the scaffold comprises stainless steel, titanium, or alloys thereof.

23. The pump of claim 21, wherein the proximal and distal ends of the scaffold are tapered.

24. The pump of claim 21, wherein the distal end comprises an inlet for blood flow during the fill stroke.

25. The pump of claim 21, wherein the proximal end comprises an outlet for blood flow during the pump stroke.

26. The pump of claim 1, wherein the housing has a diameter ranging from about 12 mm to about 20 mm in the expanded configuration.

27. The pump of claim 1, further comprising a cannula.

28. The pump of claim 27, wherein the cannula extends from the proximal end of the expandable housing.

29. The pump of claim 27, wherein the cannula extends from the distal end of the expandable housing.

30. The pump of claim 27, wherein the cannula has a length of about 2.5 cm to about 5.0 cm.

31. The pump of claim 27, wherein the cannula has a length of about 25 cm to about 30 cm.

32. The pump of claim 27, wherein the cannula has a length of about 35 cm to about 40 cm.

33. The pump of claim 1, wherein the housing further comprises a polymer layer.

34. The pump of claim 33, wherein the polymer layer comprises an elastomeric polymer.

35. The pump of claim 34, wherein the elastomeric polymer comprises a silicone, a polyester, a polyurethane, or a combination thereof.

36. The pump of claim 21, wherein the housing further comprises a fabric layer coupled to the scaffold.

37. The pump of claim 36, wherein the fabric layer comprises a woven material.

38. The pump of claim 1, wherein the valve member comprises a flexible diaphragm, the flexible diaphragm comprising a diaphragm body.

39. The pump of claim 38, wherein the flexible diaphragm comprises an elastomeric polymer.

40. The pump of claim 39, wherein the elastomeric polymer comprises a silicone, a polyester, a polyurethane elastomer, or a combination thereof.

41. The pump of claim 38, wherein the diaphragm body and the rim comprise the same material.

42. The pump of claim 38, wherein the diaphragm body and the rim are integrally formed.

43. The pump of claim 42, wherein a thickness of the rim is greater than a thickness of the diaphragm body.

44. The pump of claim 38, wherein the diaphragm body has a thickness ranging from about 0.03 mm to about 0.3 mm.

45. The pump of claim 38, wherein the rim has a thickness ranging from about 0.20 mm to about 1.5 mm.

46. The pump of claim 38, wherein the flexible diaphragm is in the collapsed configuration during the fill stroke.

47. The pump of claim 38, wherein the flexible diaphragm is in the extended configuration during the pump stroke.

48. The pump of claim 38, wherein the flexible diaphragm has a conical shape in the extended configuration.

49. The pump of claim 48, wherein the flexible diaphragm comprises a plurality of ribs that extend from a center portion of the diaphragm body to the rim.

50. The pump of claim 49, wherein a rib angle between a rib of the plurality of ribs and an axis perpendicular to the actuator ranges from about 30 degrees to about 60 degrees.

51. The pump of claim 49, wherein the plurality of ribs are equally spaced from one another.

52. The pump of claim 38, further comprising a plurality of tines coupled to the actuator that support the flexible diaphragm in the extended configuration during the pump stroke.

53. The pump of claim 52, wherein the plurality of tines are flexible and have an expanded configuration and a compressed configuration.

54. The pump of claim 1, wherein the housing comprises a plurality of openings.

55. The pump of claim 54, wherein the housing comprises between about 2 to about 25 openings.

56. The pump of claim 54, wherein the plurality of openings are equally spaced on a portion of the housing.

57. The pump of claim 54, wherein the plurality of openings are provided in a pattern on a portion of the housing.

58. The pump of claim 54, further comprising a skirt coupled to the housing and surrounding the plurality of openings.

59. The pump of claim 54, wherein the plurality of openings have a diameter ranging between about 0.10 mm to about 6.50 mm.

60. A method of pumping blood comprising:
advancing a pump to a target location within the circulatory system of a patient, the pump comprising a housing comprising an interior surface, an expanded configuration, and a collapsed configuration, and a valve member comprising a rim disposed within the housing, wherein the valve member has an extended or expanded configuration, and a collapsed configuration;
expanding the housing from the collapsed configuration to the expanded configuration at the target location;
linearly reciprocating the valve member within the housing to generate a fill stroke and a pump stroke; and
maintaining contact between the rim of the valve member and the interior surface of the housing during the pump stroke.

61. The method of claim 60, wherein the valve member comprises a valve cone, the valve cone comprising a flow control layer.

62. The method of claim 61, wherein the flow control layer comprises a plurality of flaps having an open configuration and a closed configuration.

63. The method of claim 60, wherein the valve member comprises a flexible diaphragm, the flexible diaphragm having an extended configuration and a collapsed configuration.

64. The method of claim 60, wherein the pump stroke pulls blood into the housing.

65. The method of claim 64, wherein the blood is pulled into the housing from the left ventricle.

66. The method of claim 64, wherein the blood is pulled into the housing from the aorta.

67. The method of claim 60, wherein the pump stroke pushes blood out of the housing.

68. The method of claim 67, wherein the blood is pushed out of the housing into a portion of the aorta.

69. The method of claim 68, wherein the portion of the aorta is the ascending aorta.

70. The method of claim 68, wherein the portion of the aorta is the descending aorta.

71. The method of claim 62, further comprising opening the plurality of flaps to the open configuration during the fill stroke.

72. The method of claim 62, further comprising closing the plurality of flaps to the closed configuration during the pump stroke.

73. The method of claim 63, further comprising collapsing the flexible diaphragm to the collapsed configuration during the fill stroke.

74. The method of claim 63, further comprising extending the flexible diaphragm to the extended configuration during the pump stroke.

75. The method of claim 60, wherein the housing is advanced through the aortic valve and into the left ventricle of the patient.

76. The method of claim 60, wherein the pump further comprises a cannula, and the cannula is advanced through the aortic valve and into the left ventricle of the patient.

77. The method of claim 60, wherein the target location for the housing is the aortic arch.

78. The method of claim 60, wherein the target location for the housing is the descending aorta.

79. The method of claim 60, wherein the target location for the housing is the thoracic aorta.

80. The method of claim 60, wherein the target location for the housing is the abdominal aorta.

81. The method of claim 63, wherein the pump further comprises a plurality of tines that support the flexible diaphragm in the extended configuration during the pump stroke.

82. The method of claim 60, wherein the housing comprises a plurality of openings.

83. The method of claim 82, wherein blood exiting the openings is directed in a retrograde direction toward the head of the patient during the pump stroke by a skirt coupled to the housing.

84. The method of claim 83, wherein the length of the skirt is adjusted to achieve a predetermined amount of retrograde blood flow toward the head of the patient.

85. The method of claim 83, wherein the number of openings is adjusted to achieve a predetermined amount of retrograde blood flow toward the head of the patient.

86. The method of claim 83, wherein the diameter of the openings is adjusted to achieve a predetermined amount of retrograde blood flow toward the head of the patient.

87. The method of claim 83, wherein about 60% of the blood from the pump stroke flows in a retrograde direction toward the head of the patient.

88. The method of claim 83, wherein about 50% of the blood from the pump stroke flows in a retrograde direction toward the head of the patient.

89. The method of claim 83, wherein about 40% of the blood from the pump stroke flows in a retrograde direction toward the head of the patient.

90. A method of pumping blood comprising:
advancing a pump to a target location within the aorta of a patient, the pump comprising a housing including an interior surface, an expanded configuration, and a collapsed configuration, and a valve member comprising a rim disposed within the housing, wherein the valve member has an extended or expanded configuration, and a collapsed configuration, and wherein the rim of the valve member is configured to maintain contact with the interior surface of the housing during a pump stroke;
pulling a fill volume of blood into the pump during a fill stroke; and
pushing an exit volume of blood out of the pump during the pump stroke, the exit volume comprising a first portion of blood and a second portion of blood, wherein the first portion of blood is pumped in a retrograde direction toward the head of the patient, and the second portion of blood is pumped in an anterograde direction.

91. The method of claim 90, wherein the fill stroke pulls blood from the left ventricle of the patient.

92. The method of claim 90, wherein the second portion of blood is about 60% of the exit volume.

93. The method of claim 90, wherein the second portion of blood is about 50% of the exit volume.

94. The method of claim 90, wherein the second portion of blood is about 40% of the exit volume.

95. The method of claim 90, wherein the target location is the thoracic aorta.

96. The method of claim 90, wherein the target location is the abdominal aorta.

* * * * *